US008232096B2

(12) United States Patent
Barbera-Guillem

(10) Patent No.: US 8,232,096 B2
(45) Date of Patent: Jul. 31, 2012

(54) BIOREACTOR FOR SELECTIVELY CONTROLLING THE MOLECULAR DIFFUSION BETWEEN FLUIDS

(76) Inventor: Emilio Barbera-Guillem, Powell, OH (US)

( * ) Notice: Subject to any disclaimer, the term of this patent is extended or adjusted under 35 U.S.C. 154(b) by 476 days.

(21) Appl. No.: 12/389,523

(22) Filed: Feb. 20, 2009

(65) Prior Publication Data

US 2009/0202400 A1    Aug. 13, 2009

(51) Int. Cl.
*C12M 3/00* (2006.01)
(52) U.S. Cl. ............ 435/293.1; 210/436; 210/150; 210/206; 210/120; 435/286.6; 435/289.1; 435/294.1
(58) Field of Classification Search ............ 435/286.6, 435/293.1, 294.1, 288.5; 422/82, 129, 503; 210/120, 150, 206, 436
See application file for complete search history.

(56) References Cited

U.S. PATENT DOCUMENTS

| | | | | |
|---|---|---|---|---|
| 6,322,753 | B1 * | 11/2001 | Lindberg et al. | 422/503 |
| 2002/0151078 | A1 * | 10/2002 | Kellogg et al. | 436/45 |
| 2004/0029266 | A1 * | 2/2004 | Barbera-Guillem | 435/297.5 |
| 2006/0180529 | A1 * | 8/2006 | Barbera-Guillem | 210/120 |

OTHER PUBLICATIONS

International Search Report and Written Opinion of the International Searching Authority for International Application No. PCT/US10/24471, mailed Apr. 5, 2010, 8 pages.

* cited by examiner

*Primary Examiner* — William H Beisner
*Assistant Examiner* — Michael Hobbs
(74) *Attorney, Agent, or Firm* — Michael J. Gallagher; David J. Dawsey; Gallagher & Dawsey Co., LPA

(57) ABSTRACT

A diffusion controlling bioreactor that selectively controls the molecular diffusion between fluids through at least one microchannel in fluid communication with a reaction reservoir. Length and cross-sectional area of the microchannel may be selected to obtain a predetermined rate of molecular diffusion between fluids. When the fluids are liquids, flow through the microchannel is laminar and the capillary action of the microchannel and fluid is such that the fluid flow is regulated, and may have a structure configured to minimize the chances of fluid leakage from the bioreactor, even if the bioreactor is turned in various directions. In certain embodiments, one or more diffusion control chambers regulate fluid flow and diffusion between a reaction reservoir and an outside atmosphere.

22 Claims, 39 Drawing Sheets

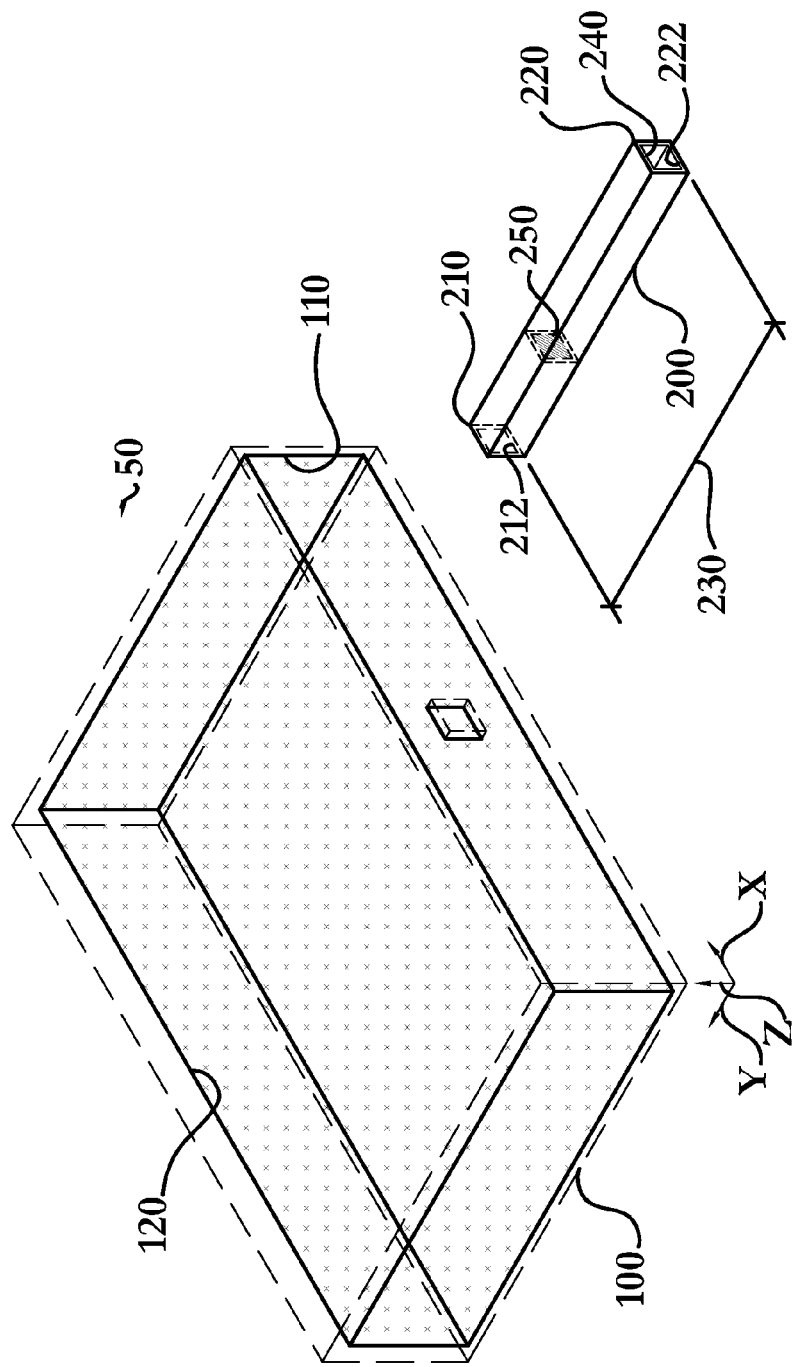
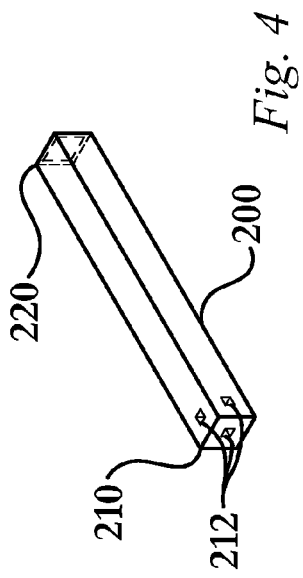

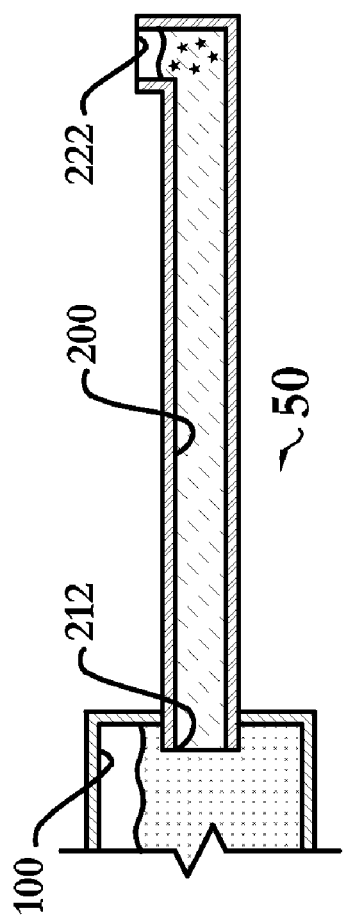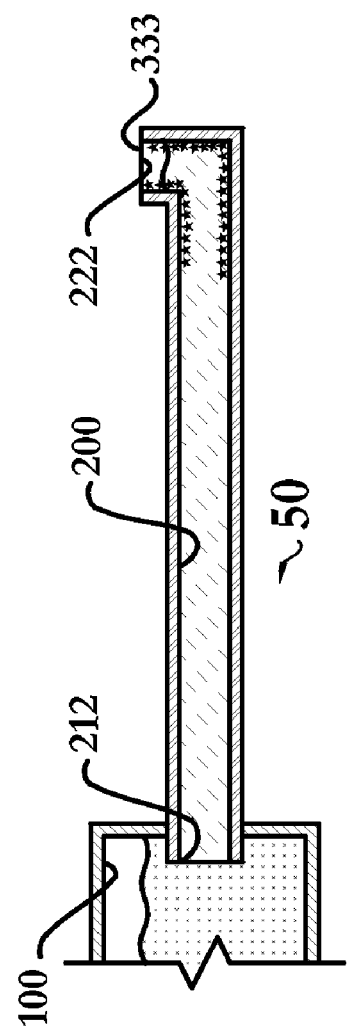

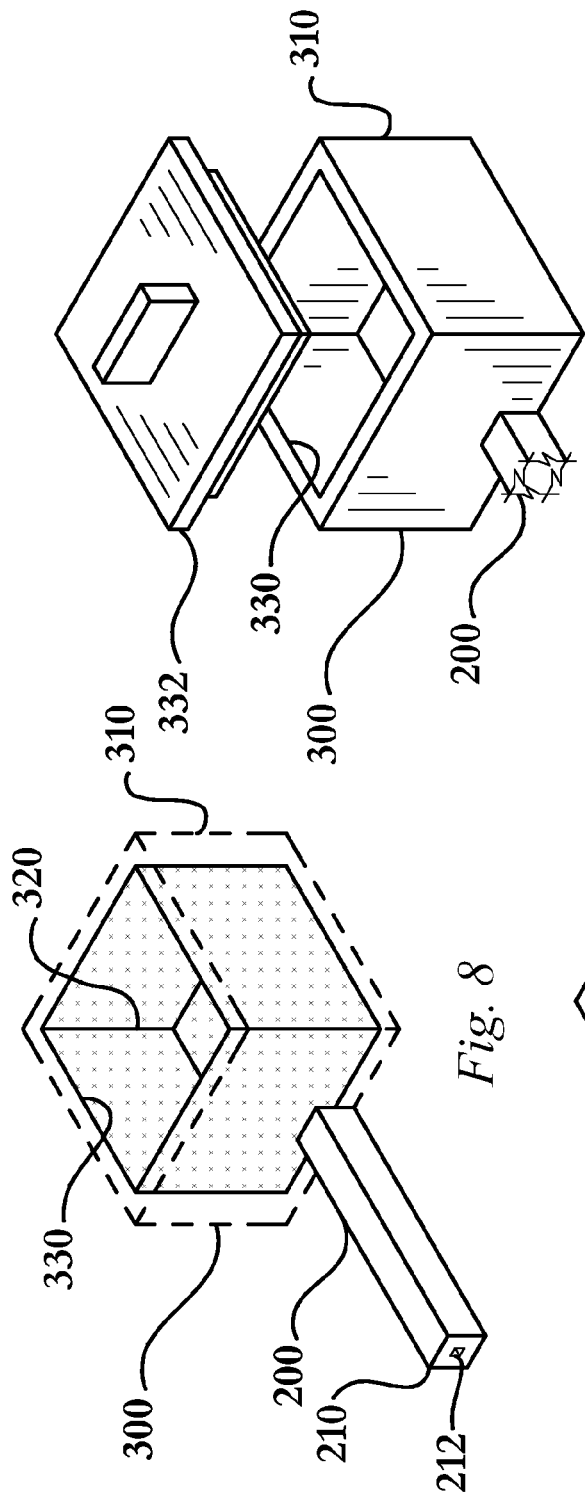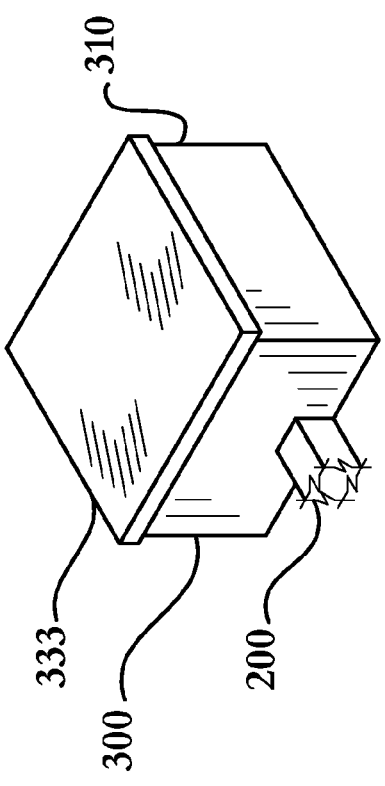

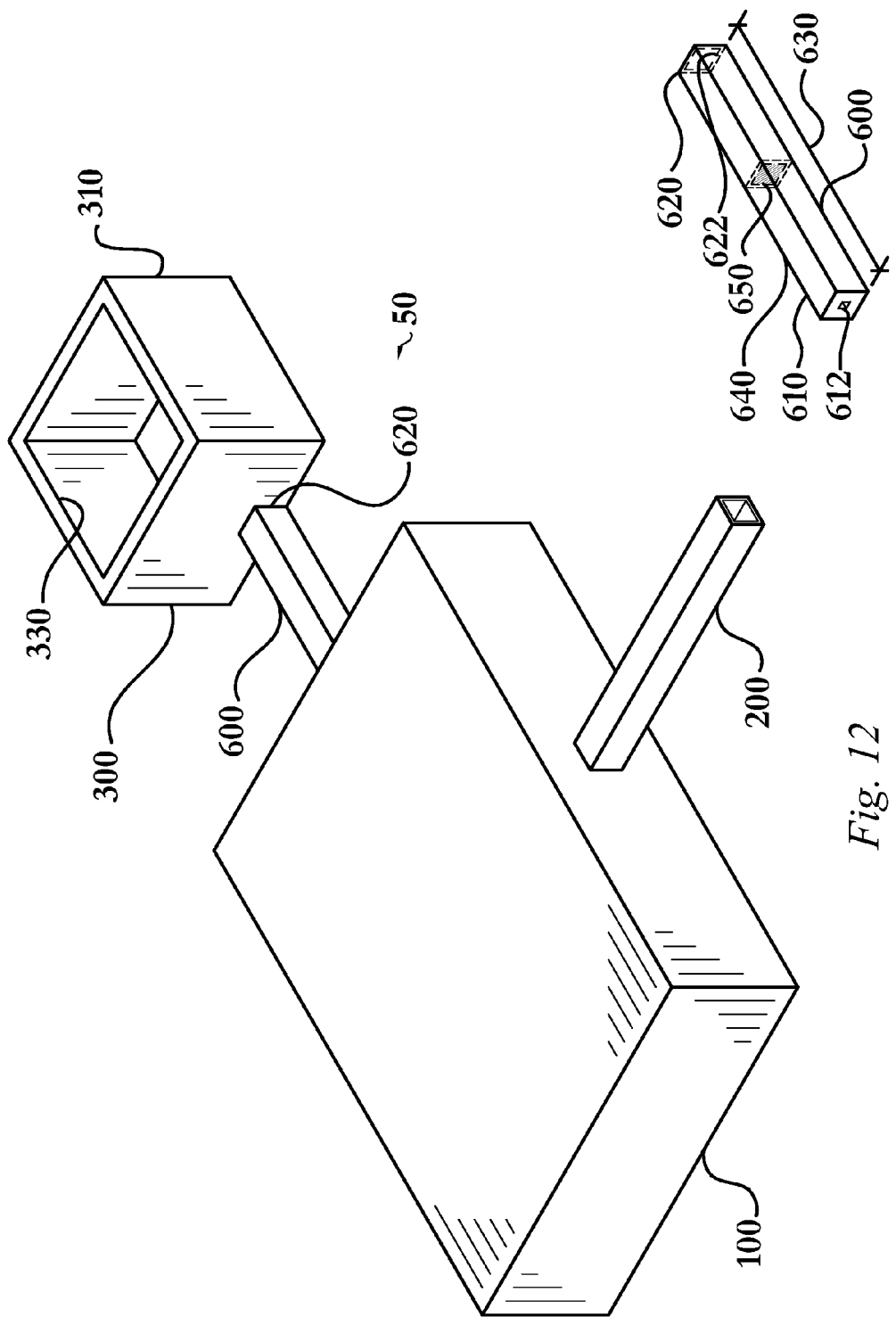

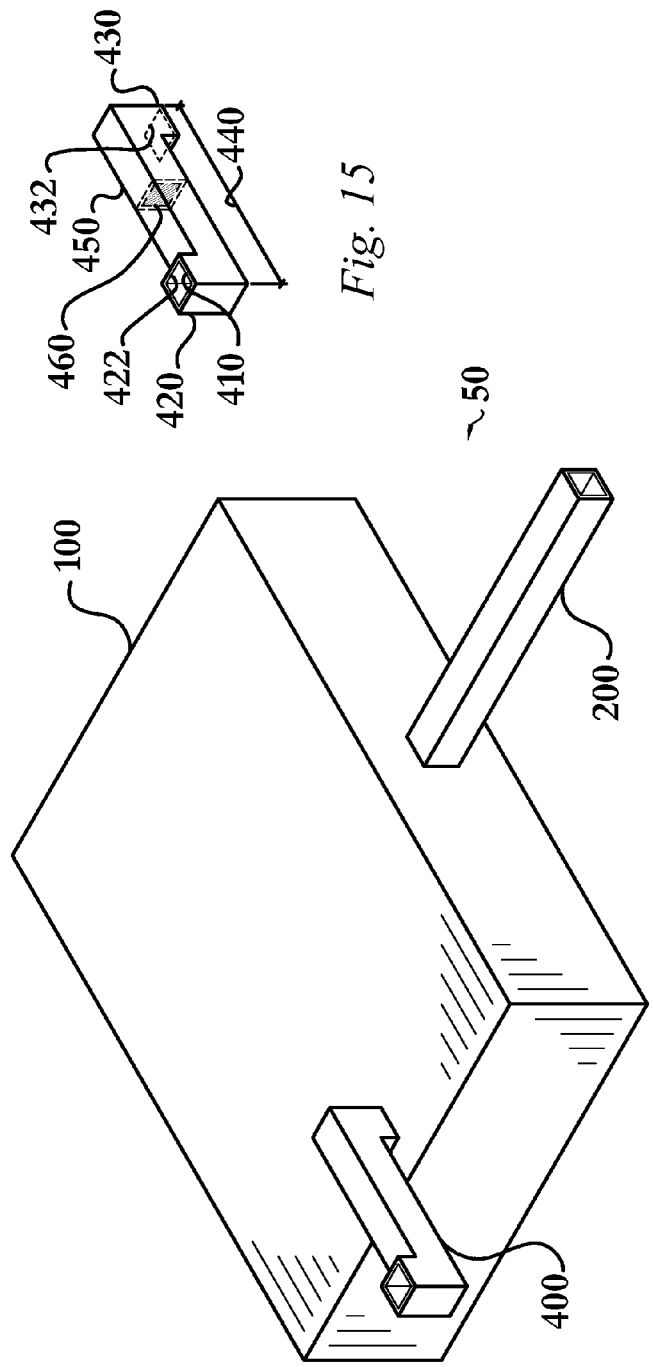
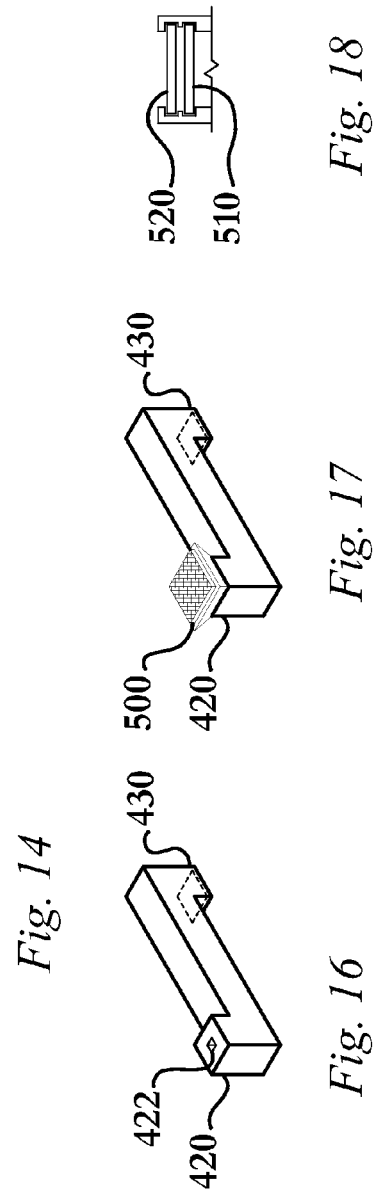

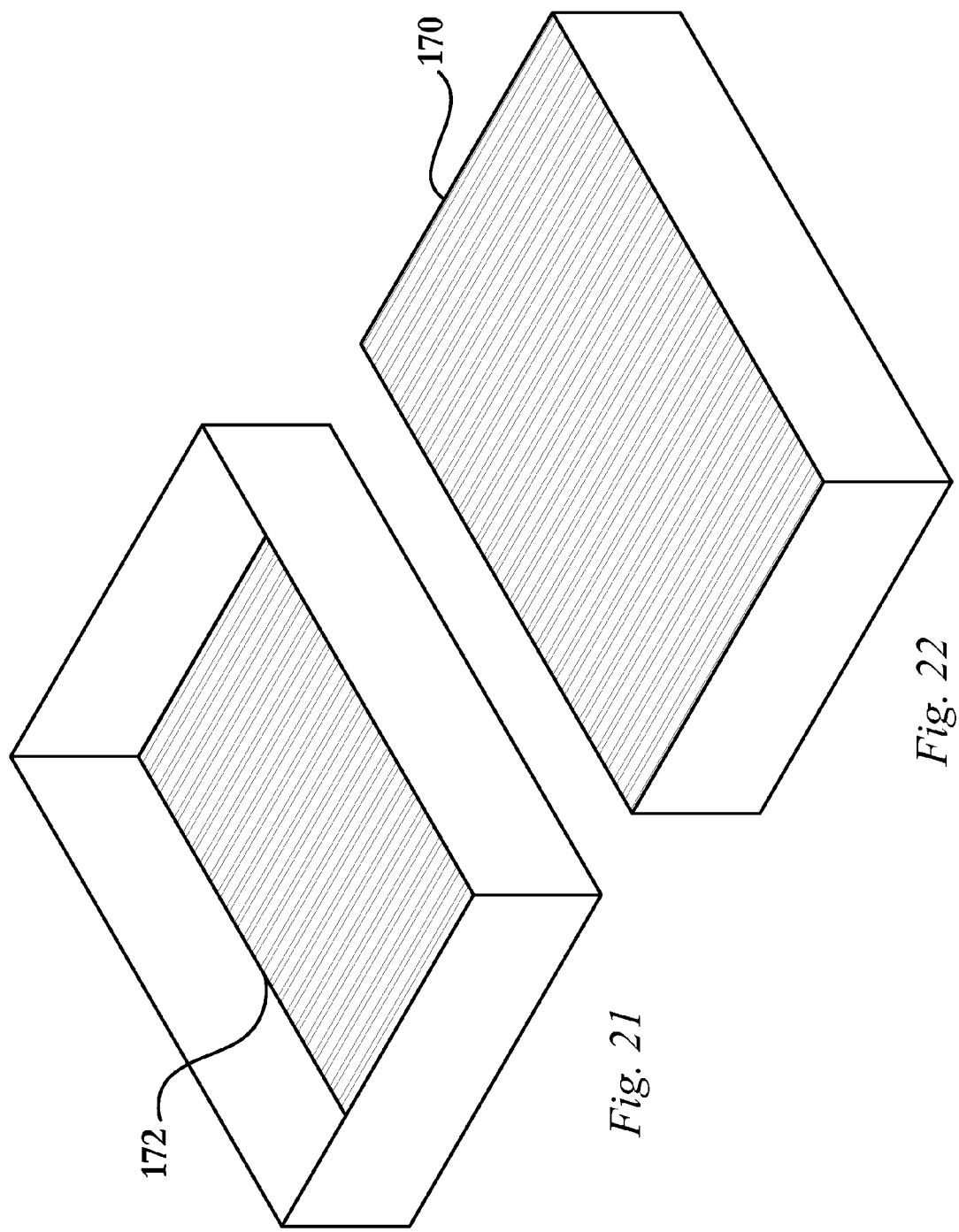

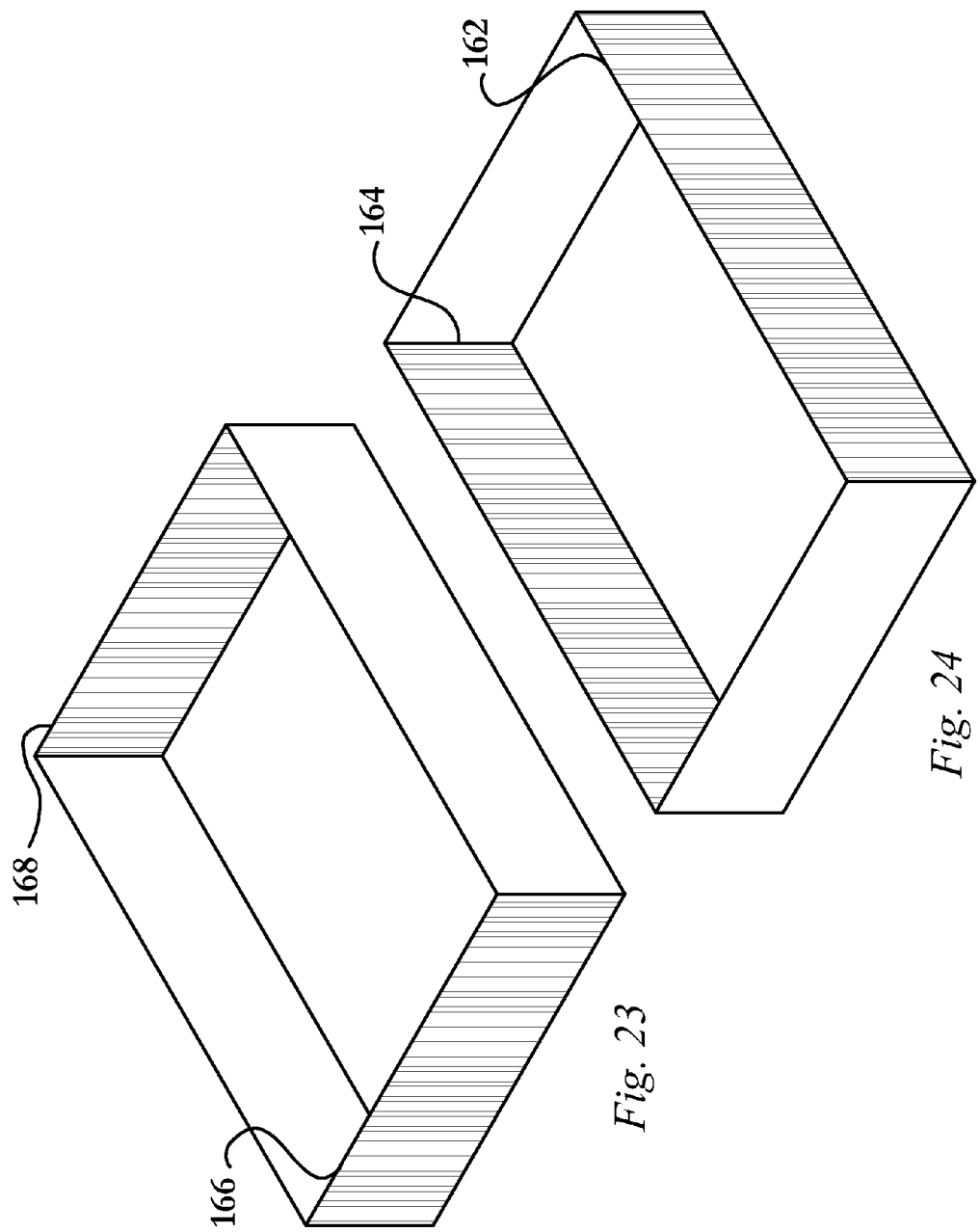

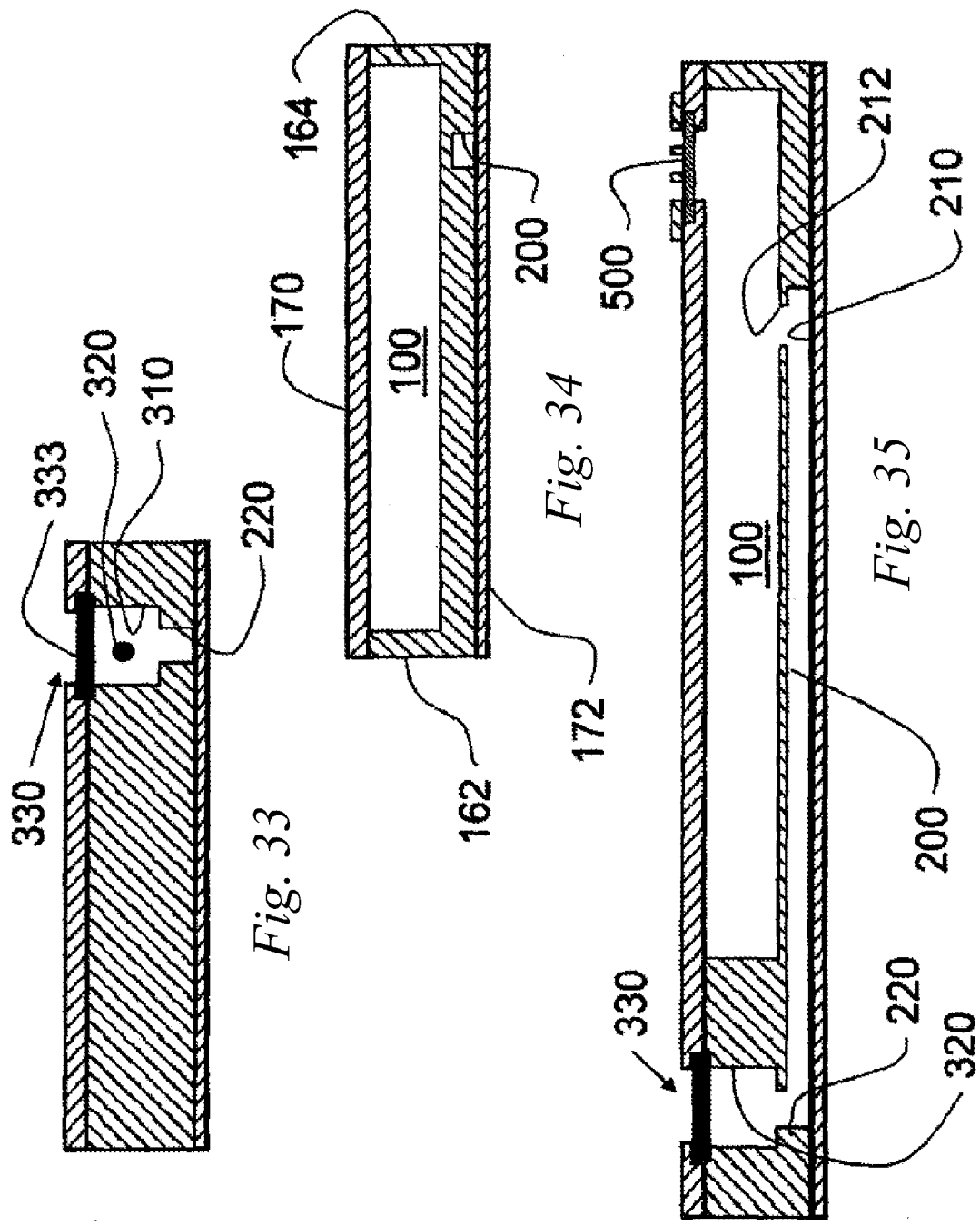

BIOREACTOR FOR SELECTIVELY CONTROLLING THE MOLECULAR DIFFUSION BETWEEN FLUIDS

STATEMENT REGARDING FEDERALLY SPONSORED RESEARCH OR DEVELOPMENT

This invention was not made as part of a federally sponsored research or development project.

TECHNICAL FIELD

The instant invention relates to a bioreactor for selectively controlling the molecular diffusion between fluids, particularly, to a bioreactor capable of very slow transfers of molecules into and out of the bioreactor by utilizing the Brownian motion of the molecules in given fluids.

BACKGROUND OF THE INVENTION

Bioreactors are common laboratory and industrial installations used in the areas of cell culture, chemical production, fermentation, testing and analysis, and other biological processes well known to those skilled in the art. A problem inherent in such bioreactors is the need to control the ingress and egress of various compounds to and from the bioreactor. As the size and volume of bioreactors decrease, or as the need to control becomes increasingly exacting, problems occur in the need to precisely control, over a long period of time or in respect of very small quantities of certain compounds, the movement of molecules both into and out of the bioreactor.

Various means have been employed to control small flows of fluids, in a field generally called microfluidics. In general, the means have proposed mechanical devices that are designed to mechanically, but accurately, deliver very small amounts of a fluid through various microchannels to a delivery point. A typical example is seen in U.S. Pat. No. 6,810,713; in which rotors periodically squeeze the microchannels formed in an elastic polymeric substrate to propel small amounts of fluid towards a delivery point by their compressive effect on the microchannel. Another approach is seen in U.S. Pat. No. 6,797,187; in which an electromagnetic field is used to generate a flow of a fluid in a microchannel lined, at least in part, with silicon nitride. Yet another approach is seen in U.S. Pat. No. 6,743,636; wherein pneumatically driven Venturi pumps move fluid through a microchannel system.

These approaches, and others that form the present art, rely on the movement of fluid volumes, albeit small ones, in order to transfer the various components that may be present in such fluids. Therefore, they fall prey to a myriad of problems. As the scale of the device decreases, it becomes increasingly difficult for a mechanical, or even electro-mechanical, device to control the very slow movement of molecules. Even slight variations in the operation of the various pumping mechanisms will result in wide swings, in a relative sense, in the amount of fluids transferred. The instant invention, on the other hand, is novel in its approach to controlling the displacement of various molecules into and out of a bioreactor system by controlling the rate of diffusion at an interface between two fluids, while minimizing any actual mixing of the fluids themselves. Therefore, the delivery of various molecules is inherently stable and predictable, and simple variations in the structure of the bioreactor suffice to control this diffusion.

SUMMARY OF INVENTION

In its most general configuration, the present invention advances the state of the art with a variety of new capabilities and overcomes many of the shortcomings of prior devices in new and novel ways. In its most general sense, the present invention overcomes the shortcomings and limitations of the prior art in any of a number of generally effective configurations.

In one configuration, the present invention relates to a method of using principles of diffusion to control the transfer of molecules into and out of a bioreactor. Diffusion is a reflection of the fact that molecules, as they vibrate with random motion, called Brownian motion, in a gas or liquid, move toward an equilibrium state where all the molecules in the mixture are uniformly dispersed, and the concentration of any molecular species is the same everywhere.

The diffusion equation (Fick's second law), states that the rate of molecular diffusion is proportional to the second derivative of its concentration. This can be written:

$$\frac{\partial C}{\partial t} = D \frac{\partial^2 C}{\partial x^2}$$

wherein C is the concentration, t is the time, and x is the distance.

FIG. 1 illustrates a diffusion model for a diffusion gradient along a long axis x, with diffusion progressing in the direction of the arrows. In a laminar flow state, the concentration of the diffusing substance will be equal at all points on a given plane orthogonal to the direction of laminar flow, illustrated as a first plane J1 and a second plane J2. In summary, given a theoretical scheme for diffusion between two compartments separated by a distance (x), as seen in FIG. 1, the diffusion equation could be expressed as:

$$\frac{\partial C_B}{\partial t} = D_B \frac{\partial^2 C_B}{\partial x^2} \bigg|$$

Thus; to reach a certain concentration at plane $J_2$, given a concentration at plane $J_1$ of $C_B$, as seen in FIG. 1, the following variables will determine the diffusion between the planes:
1) Distance between planes $J_1$ and $J_2$ (x).
2) Time (t); and
3) Diffusion coefficient of the molecule ($D_B$), which will be constant for a given molecule for each specific fluid viscosity and temperature.

Therefore, for a given system the combination of distance and time will determine the rate of passage of a molecule from a first location, such as a point on plane J1 to a second location, such as a point on plane J2. The magnitude of molecular diffusion will be a function of both distance and time, along with the interface's surface area, that is, the area available for diffusion. Consequently, it is possible to control time of passage from a first location to a second location of a certain amount of a given molecule by setting the other four variables: surface area of the interface, fluid viscosity, temperature, and distance between the locations.

Contemplation will show that since the rate of diffusion is inversely related to the square of the distance between the compartments (x), relatively small increases in distance will have a large effect in slowing the rate of diffusion; and relatively large increases in distance will have an extremely large effect in slowing the rate of diffusion. The calculation of the rate of diffusion in both time and distance is complex; as an application of Fick's second law of diffusion, which can be expressed as follow for long distances:

$$\frac{dC}{dx} = -\frac{C_s}{\sqrt{\pi Dt}} \exp\left\{\frac{-x^2}{4Dt}\right\}$$

where C=concentration of substance in question, t=the time of diffusion, x=distance, Cs=starting concentration, and D=coefficient of diffusion for the molecule in the fluid.

A fast estimate of the rate of diffusion can be realized from the simpler relation that the time, (t), for 37% of the molecules to diffuse over the given distance, x, can be simply calculated as:

$$t = x^{D/2}$$

The figure of 37% comes from the fact that the process is exponential, e (the base of natural logs)=2.7183, therefore 1/e=0.37, or 37%. This calculation is for the simplest solution for diffusion in one dimension away from a plane. Note that as observed above, the time required for diffusion of a given quantity increases with the square of the distance.

In order to visualize the important effect of distance (x) in determining the rate of diffusion for a given molecule and fluid, one may compare illustrative applications. In a system where the fluid is water, the diffusing molecules are oxygen, and the system is maintained at 37° C., as seen in Table 1; the time value for 37% oxygen diffusion across three different spaces is calculated, each reflecting a difference in diffusion distance (x). The applications are diffusion: (a) across lung epithelium (having an average thickness of $5 \times 10^{-7}$ m); (b) from the atmosphere to the cell layer in a typical laboratory T flask (where the cell layer is separated from the atmosphere by an average distance of 0.003 m); and (c) from the atmosphere to the fluid inside an innovative bioreactor in which the principles of the instant invention are utilized to create a nearly one meter separation between the external environment and the reservoir of fluid within the device.

TABLE 1

|   | x (m) | Oxygen D | Time sec | Days |
|---|---|---|---|---|
| a | $5 \times 10^{-7}$ | $1.8 \times 10^{-9}$ | 0.000035 | 0.00 |
| b | 0.003 | $1.8 \times 10^{-9}$ | 1,250 | 0.01 |
| c | 0.98 | $1.8 \times 10^{-9}$ | 133,388,889 | 1543.85 | x = distance in meters, D = coefficient of diffusion in water

Therefore, it is evident that by increasing the distance between compartments, it is possible to greatly slow diffusion, to a point at which diffusion becomes so slow that, for practical purposes, it stops. Therefore, by manipulating the separation between compartments in a bioreactor, as by way of example and not limitation, extending a long tube between otherwise separated compartments, it is possible to delay diffusion. Manipulation of the length of the tubing will control the rate of diffusion, if other variables are held steady and the movement of fluid is prevented. Nearing the extreme upward limit of delay mentioned above, such a system, as seen in various embodiments of the instant invention, can serve to create a virtual hermetic seal through which, on a practical basis, diffusion times are so long that there is effectively no movement of particular molecules from one end of the seal to the other. In other words, if sufficient distance is created, diffusion becomes so slow that it may be disregarded.

In a preferred embodiment, the instant invention includes a diffusion controlling bioreactor that selectively controls the molecular diffusion between a first fluid and a second fluid. The diffusion controlling bioreactor includes a microchannel in fluid communication with a reaction reservoir. The length and cross-sectional area of the microchannel are selected to obtain a predetermined rate of molecular diffusion between the first fluid and the second fluid. The flow of fluid through the microchannel is laminar and the capillary action of the microchannel and the fluid is such that the fluid does not flow into the reaction reservoir unless the pressure of the fluid is increased by an external source, which may or may not include the effects of gravity on the fluids.

In one of the applications of the instant invention, a microchannel may be configured of such a length and cross-sectional area that, when the microchannel is used to connect the filling means of the bioreactor with the reaction reservoir, microorganisms that may inadvertently contaminate the filling means of the bioreactor are prevented from successfully traversing the microchannel. The laminar flow state of fluid in the microchannel and lack of fluid flow into the reaction reservoir results in non-motile organisms failing to reach the reaction reservoir in generally applicable time frames, and the slow diffusion of nutrients and oxygen from the reaction reservoir toward such organisms results in the death of these organisms before they can diffuse or extend by colony growth to the bioreactor.

In addition to the ability to virtually "seal" the bioreactor from contaminants, the instant invention may utilize at least one microchannel and reagent reservoir to effect and regulate, rather than prevent, the passage of various molecules into the reaction reservoir of the bioreactor. For instance, various substances such as drugs in varying concentrations, nutrients, or other agents, may be introduced into the reagent reservoir in the form of a first fluid, which is in fluid communication through the microchannel to the reaction reservoir, which contains a second fluid. The microchannel is sized to have a length and cross-sectional area that may predetermine a rate of diffusion for such substances into the reaction reservoir. The user fills the microchannel and the reagent reservoir only sufficiently to advance the first fluid to the proximal end of the microchannel. At that point, as long is there is a difference in viscosity between the first and second fluid, and unless the microchannel is pressurized above or below the pressure of the reaction reservoir, there will be no movement of fluid between the microchannel and the reaction reservoir, only diffusion of molecules at the interface between the fluids contained in each.

The bioreactor may further incorporate a pressure equalizing vent that operates on similar principles to the microchannel described above. The pressure equalizing vent may have a structure configured to minimize the chances of fluid leakage from the bioreactor, even if the bioreactor is turned in various directions.

In yet another embodiment, a bioreactor may include a plurality of fluid-filled structures bounded within an external frame and may include at least a first microchannel, a reaction reservoir, at least one diffusion control chamber and a second microchannel.

In a variety of additional embodiments, the previously described bioreactor may include more than one diffusion control chamber in fluid communication with the first fluid diffusion control chamber. It is specifically intended by this specification that there be no absolute upper limit on the number of diffusion control chambers.

The length of the second microchannel may vary greatly, and the second microchannel length may be determined, by one skilled in the art, to accomplish certain bioreactor structural and diffusion rate goals.

Within the diffusion control chamber, diffusion control chamber fluid flow control ports may be configured to have an area of reduced sidewall thickness sufficient to minimize formation of a meniscus at the first diffusion control chamber fluid flow control ports by a fluid within the at least first diffusion control chamber. Additionally, at least one of the diffusion control chamber fluid flow control ports may block the flow of a fluid through the diffusion control chamber fluid flow control port when the pressure of the fluid is not increased by an external source and there is a difference in viscosity between the fluid in the diffusion control chamber and a fluid outside of the diffusion control chamber. It is further specifically intended by this specification that there be no absolute upper limit on the number of diffusion control chamber fluid flow control ports so configured.

Numerous alterations, modifications, and variations of the preferred embodiments disclosed herein will be apparent to those skilled in the art and they are all anticipated and contemplated to be within the spirit and scope of the instant invention. For instance, it is understood that the specification of a first fluid, a second fluid, and a third fluid are for illustration, and not limitation, only. The fluids may all be of the same composition, or may be different. Additionally, the illustration of particular features in various embodiments is for illustration only, and not limitation. Any or all of the various features of the instant invention maybe combined in various illustrated and non-illustrated embodiments, as would be known to one skilled in the art. Further, although specific embodiments have been described in detail, those with skill in the art will understand that the preceding embodiments and variations can be modified to incorporate various types of substitute and/or additional or alternative materials, relative arrangement of elements, and dimensional configurations. Accordingly, even though only few variations of the present invention are described herein, it is to be understood that the practice of such additional modifications and variations and the equivalents thereof, are within the spirit and scope of the invention as defined in the following claims. The corresponding structures, materials, acts, and equivalents of all means or step plus function elements in the claims below are intended to include any structure, material, or acts for performing the functions in combination with other claimed elements as specifically claimed.

BRIEF DESCRIPTION OF THE DRAWINGS

Without limiting the scope of the present invention as claimed below and referring now to the drawings and figures:

FIG. 3 shows detail of the embodiment of the bioreactor of FIG. 2 in elevated perspective view, not to scale, with the microchannel shown separated from the reaction reservoir for clarity;

FIG. 4 shows a variation of the detail of the microchannel of the bioreactor of FIG. 2 in elevated perspective view;

FIG. 5 shows a cross-section view of a microchannel of the bioreactor of FIG. 2;

FIG. 6 shows a cross-section view of a microchannel of the bioreactor of FIG. 2;

FIG. 8 shows a portion of the embodiment of the bioreactor of FIG. 7 in elevated perspective view;

FIG. 9 shows a portion of another embodiment of the bioreactor of FIG. 7 in elevated perspective view;

FIG. 10 shows a portion of another embodiment of the bioreactor of FIG. 7 in elevated perspective view;

FIG. 12 shows another embodiment of the bioreactor of the instant invention in elevated perspective view;

FIG. 13 shows a portion of the embodiment of the bioreactor of FIG. 12 in elevated perspective view;

FIG. 14 shows another embodiment of the bioreactor according to the instant invention in elevated perspective view;

FIG. 15 shows a portion of the embodiment of the bioreactor of FIG. 14 in elevated perspective view;

FIG. 16 shows a portion of another embodiment of the bioreactor of FIG. 14 in elevated perspective view;

FIG. 17 shows a portion of another embodiment of the bioreactor of FIG. 14 in elevated perspective view;

FIG. 18 shows a portion of the embodiment of the bioreactor of FIG. 17 in elevated perspective view;

FIG. 21 shows detail of a surface of the bioreactor of the instant invention in elevated perspective view;

FIG. 22 shows detail of a surface of the bioreactor of the instant invention in elevated perspective view;

FIG. 23 shows detail of two surfaces of the bioreactor of the instant invention in elevated perspective view;

FIG. 24 shows detail of two surfaces of the bioreactor of the instant invention in elevated perspective view;

FIG. 33 shows a cross-section view of the bioreactor of FIG. 32 viewed across section line A-A in FIG. 32;

FIG. 34 shows a cross-section view of the bioreactor of FIG. 32 viewed across section line B-B 9 in FIG. 32;

FIG. 35 shows a cross-section view of the bioreactor of FIG. 32 viewed across section line C-C in FIG. 32;

Figure 1:
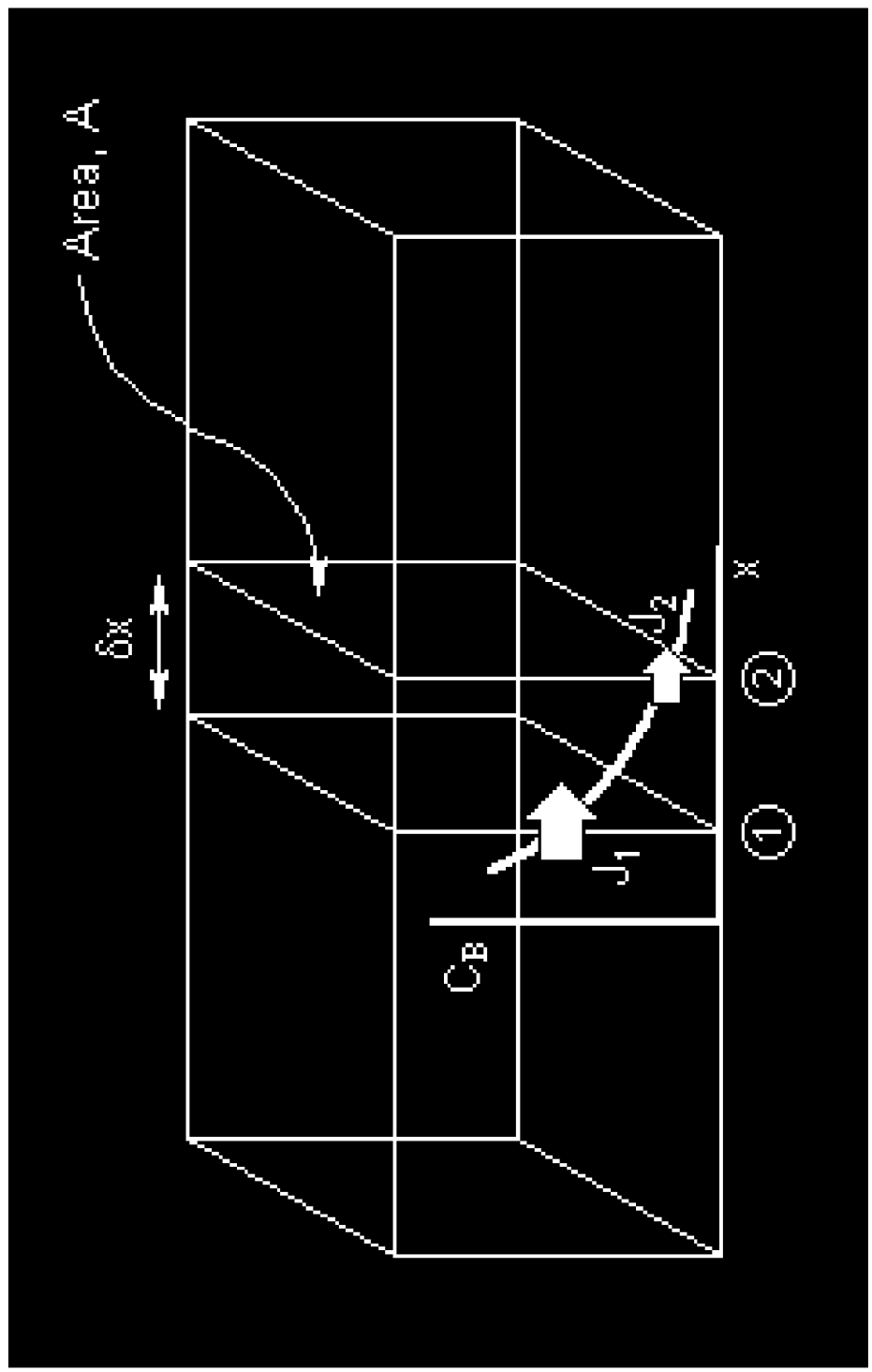
FIG. 1 shows a diffusion model illustrating a diffusion process in a laminar flow state proceeding in the direction of the arrows along the long axis of the model.

These drawings are provided to assist in the understanding of the exemplary embodiments of the invention as described in more detail below and should not be construed as unduly limiting the invention. In particular, the relative spacing, positioning, sizing and dimensions of the various elements illustrated in the drawings are not drawn to scale and may have been exaggerated, reduced or otherwise modified for the purpose of improved clarity. Those of ordinary skill in the art will also appreciate that a range of alternative configurations have been omitted simply to improve the clarity and reduce the number of drawings.

DETAILED DESCRIPTION OF THE INVENTION

The method and materials of the bioreactor for selectively controlling the molecular diffusion between fluids of the instant invention enables a significant advance in the state of the art. The preferred embodiments of the method and materials accomplish this by new and novel arrangements of elements and methods that are configured in unique and novel ways and which demonstrate previously unavailable but preferred and desirable capabilities.

The detailed description set forth below in connection with the drawings is intended merely as a description of the presently preferred embodiments of the invention, and is not intended to represent the only form in which the present invention may be constructed or utilized. The description sets forth the designs, functions, means, and methods of implementing the invention in connection with the illustrated embodiments. It is to be understood, however, that the same or equivalent functions and features may be accomplished by different embodiments that are also intended to be encompassed within the spirit and scope of the invention.

Figure 2:
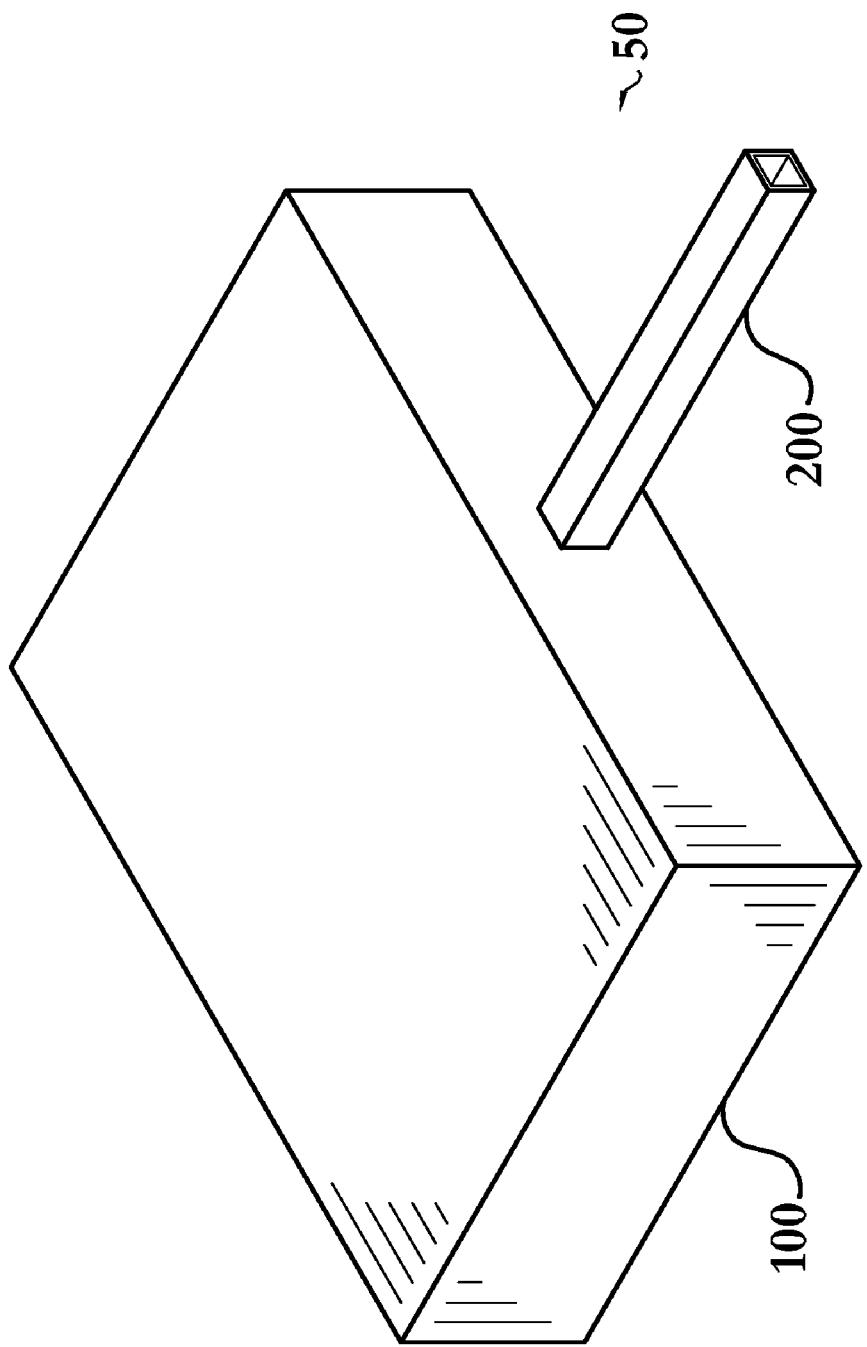
FIG. 2 shows an embodiment of a bioreactor according to the instant invention in elevated perspective view.

In a preferred embodiment, seen in FIGS. 2 through 4, the instant invention includes a diffusion controlling bioreactor (50) that selectively controls the molecular diffusion between a first fluid and a second fluid, and includes a reaction reservoir (100), having at least one reaction reservoir sidewall (110) that defines a reaction reservoir volume (120) and a microchannel (200). The reaction reservoir (100) initially contains the first fluid.

The microchannel (200) is in fluid communication with the reaction reservoir (100). As seen in FIG. 3, the microchannel (200) has a proximal end (210) with a proximal end opening (212), a distal end (220) with a distal end opening (222), a length (230), and at least one microchannel sidewall (240), having a sidewall thickness (245), and defining a cross-sectional area (250). The length (230) and cross-sectional area (250) are selected to obtain a predetermined rate of molecular diffusion between the first fluid in the reaction reservoir (100) and the second fluid in the microchannel (200). The microchannel (200) is configured in a manner such that when the microchannel (200) is filled with the second fluid, and the second fluid is a liquid, flow of the second fluid through the microchannel (200) is laminar. The capillary action of the microchannel (200) and the second fluid is such that the second fluid does not flow into the reaction reservoir (100) unless the pressure of the second fluid is increased by an external source, such as, by way of example and not limitation, pressurization of the microchannel caused by an increase of temperature.

Figure 27:
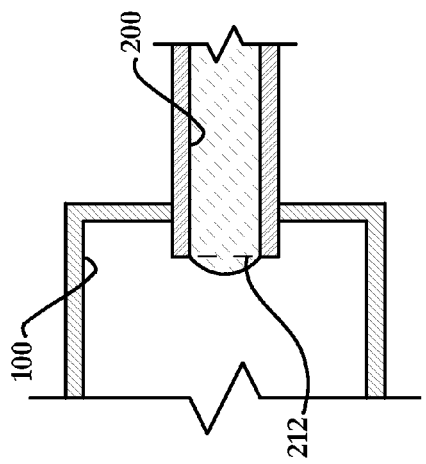
FIG. 27 shows a portion of an embodiment of the bioreactor of the instant invention in cross-sectional view.
Figure 28:
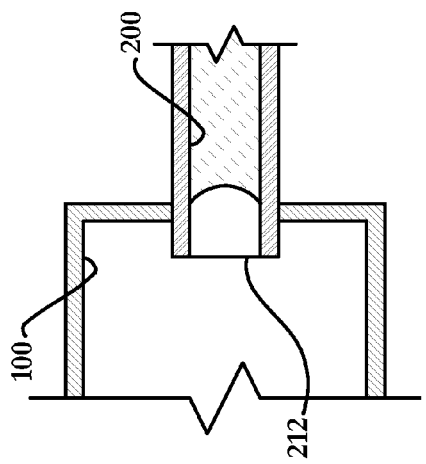
FIG. 28 shows a portion of an embodiment of the bioreactor of the instant invention in cross-sectional view.

For example, assuming that the reaction reservoir (100) is initially empty, or only contains air, as a user fills the microchannel (200) through the microchannel distal end opening (222) with a second fluid that is a liquid, the capillary action of the microchannel (200) and the second fluid results in the second fluid being drawn to the microchannel proximal end (210), as seen in FIG. 27, until the liquid reaches the proximal end opening (212), as seen in FIG. 28, where it stops. This is also the situation when the reaction reservoir (100) contains a liquid and the liquid is not soluble with the liquid that is introduced and drawn from the microchannel distal end opening (222) to the microchannel proximal end opening (212).

One illustrative embodiment of the instant invention, seen in FIGS. 5 and 6, utilizes a predetermined rate of diffusion to act as an antiseptic barrier in a diffusion controlling bioreactor (50). Contamination is a consistent problem in the laboratory and commercial uses of most bioreactors, especially in eukaryotic cell cultures. Ports, most often made of penetrable elastomeric septa, are used to introduce and remove various components from bioreactors, most often by means of a pipette-like device that first punctures the septum, and then adds or removes components from the bioreactor. The septum is designed to resealably close after withdrawal of the pipette. It is well known in the art that such punctures tend to introduce contamination into the system, by either the pipette directly introducing bacteria through the punctured septum at the time of puncture, or by the pipette leaving a very small defect, or defects after repeated use, after withdrawal of the pipette. Organisms, for example, bacteria, yeast, and fungi, eventually migrate through these very small defects.

As applied to the instant invention, the introduced organisms, represented in FIG. 5 by small stars, would tend to mix with the fluid present in the distal end (220) of the microchannel (200). Small colonies of bacteria or yeast would tend to begin growth on the interior wall of the distal end (220), or in close proximity to the distal end opening (222), as see in FIG. 5. The microchannel (200) must be sized so that only laminar flow of fluid is possible when the fluid is a liquid. As is well-known in the art, by way of example and not limitation, a microchannel (200) with a cross-sectional area of less than approximately 4 $mm^2$ will satisfy this requirement for many liquids.

Once the microchannel (200) is filled with fluid, flow stops and the microchannel remains in a laminar flow state. Should flow resume, or currents develop within the fluid, due to, by way of illustration and not limitation, agitation or heating of the fluid, the sizing of the microchannel ensures that only laminar fluid movement can take place within the microchannel. Non-motile bacteria, due to the exclusively laminar flow characteristics of the microchannel (200), are limited in their movement through the fluid present in the microchannel (200) to diffusion through the fluid. The diffusion constant of non-flagellated bacteria, as is well known in the art, is between around 0.0000001 $cm^2$/sec and 0.0000017 $cm^2$/sec. As a result, for an illustrative embodiment utilizing a microchannel (200) of the instant invention that is 10 cm long, it will take between 1 and 21 years for most bacteria to diffuse from the distal end (220) of the microchannel (200) to the reaction reservoir (100).

Additionally, living contaminants such as bacteria, yeast and fungi can be transported by direct extension, or colony growth, represented as small stars along the interior walls of the microchannel (200) near the distal end opening (222), as seen in FIG. 6. Most common organisms, certain flagellated or other motile bacteria excepted, will grow confluently in all directions from their initial point of attachment, including along the microchannel (200) of the instant invention towards the reaction reservoir (100). The fluid in the microchannel (200) may contain necessary survival requirements for all microorganisms, such as sugars and amino acids. Furthermore, the fluid may contain oxygen, a necessary requirement for the existence and growth of aerobic life forms. These required substances, if consumed by bacterial growth at the distal end (220) of the microchannel (200) will diffuse through the fluid from the reaction reservoir (100) towards the distal end (220) of the microchannel (200) at a rate predetermined by the cross-sectional area (250) and length (230) of the microchannel (200). Additionally, such growth, along with the normal metabolic needs of the undesirable organisms, will necessarily begin consuming the required substances at the distal end opening (222) of the distal end (220) of the microchannel (200).

The eventual contamination of the reaction reservoir (100) by extending organism colonies becomes a race in time for the organisms to grow to the reaction reservoir (100) before consuming the oxygen and nutrients along the route of growth through the microchannel (200), or oxygen and nutrients that the organisms can obtain due to diffusion of the nutrients and oxygen towards the organisms. The consumption and exhaustion of oxygen and nutrients will lead to stoppage of organism growth, and therefore stoppage of the migration. It therefore becomes possible for one skilled in the art, knowing the diffusion constants of such common gases as oxygen and carbon dioxide, and such common nutrients as glucose and lipids, to configure a microchannel (200) of such length (230) and cross-sectional area (250) that the resultant diffusion times of various molecules may be easily calculated. In an illustrative embodiment, the aforementioned microchannel (200) with a length (230) of 10 cm will result in a diffusion time, by the equations given in the Background of the Invention above, along the length (230) of the microchannel (200) of 36.2 days for oxygen, 42.2 days for carbon dioxide, and 85.8 days for glucose, in a water based system maintained at 37° C. Even a microchannel (200) that is significantly shorter than the preceding example will have a significant effect on diffusion time. For example, a microchannel that is only 1 cm in length (230), will have diffusion times of 8.7 hours for oxygen, 10.2 hours for carbon dioxide, and 20.6 hours for glucose, in a water based system maintained at 37° C.

Accordingly, it is highly likely that any living contaminants will perish from lack of oxygen, acidosis due to failure of the removal of carbon dioxide from the peri-cellular environment, or deprivation of nutrients, long before they can reach the reaction reservoir (100) of the instant invention, given the usual range of times during which laboratory or commercial biological processes are conducted. Therefore, as seen in FIGS. 5 and 6, the microchannel (200) tends to act as an antimicrobial barrier to contamination of the bioreactor (50), even should contaminants pass any physical barriers, such as a cap (332), or a resealable elastomeric septum (333), as seen in FIGS. 9 and 10, that may be present at the distal end opening (222) of the microchannel (200). Thus, in such an embodiment, the controlled diffusion through the microchannel (200) is used to effect a virtual "seal" between the reaction reservoir (100) and an external environment.

Again as applied to the instant invention, such a virtual "seal" may be used to limit the diffusion of gases into and out of the bioreactor (50) to that which takes place across the walls of the bioreactor. By way of example and not limitation, certain cell cultures, such as stem cells, require a carefully regulated oxygen environment. Unrestricted access by oxygen to these cells can result in cell death or transformation. The bioreactor (50) may be designed with a predetermined surface area to the walls of the bioreactor (50), and be built of a material having a predetermined diffusion constant for oxygen. In this way, the bioreactor (50) may auto-regulate the amount of oxygen available for the biological process within. Therefore, in a cell culture or similar application, the bioreactor (50) may be configured in such a manner and from such a material that a surface area of the reaction reservoir (100) (formed by the surfaces (162), (164), (166), (168), (170), and (172)) and the oxygen diffusion constant of the reaction reservoir sidewall (110) material, result in the diffusion of a predetermined amount of oxygen per unit of time, calculated to support the metabolic needs of a predetermined number of cells. By way of example and not limitation, in a cell culture application, the bioreactor (50) may be formulated of a plastic material and with a reaction reservoir surface area such that 4.6 ml of oxygen is diffused, to support the metabolic needs of approximately $2 \times 10^7$ cells, at atmospheric pressure and 37° C., per day.

In addition to the ability to virtually "seal" the bioreactor (50) from contaminants and gases, the instant invention may utilize at least one microchannel (200) and reagent reservoir (300) to promote and regulate, rather than prevent, the passage of various molecules into the reaction reservoir (100) of the bioreactor (50).

In another embodiment, as seen in FIGS. 7 through 11, there may be a reagent reservoir (300) at the distal end (220) of the microchannel (200) that is in fluid communication with both the microchannel (200) and the reaction reservoir (100). In such an embodiment, the reagent reservoir (300) has at least one reagent reservoir sidewall (310) defining a reagent reservoir volume (320), seen in FIG. 8, and has a reagent reservoir opening (330) through which the second fluid enters the reagent reservoir (300). The reagent reservoir opening (330) may be closed by a cap (332), or by a penetrable, self-sealing, elastomeric septum (333), among other methods, as seen in FIGS. 9 and 10.

Figure 11:
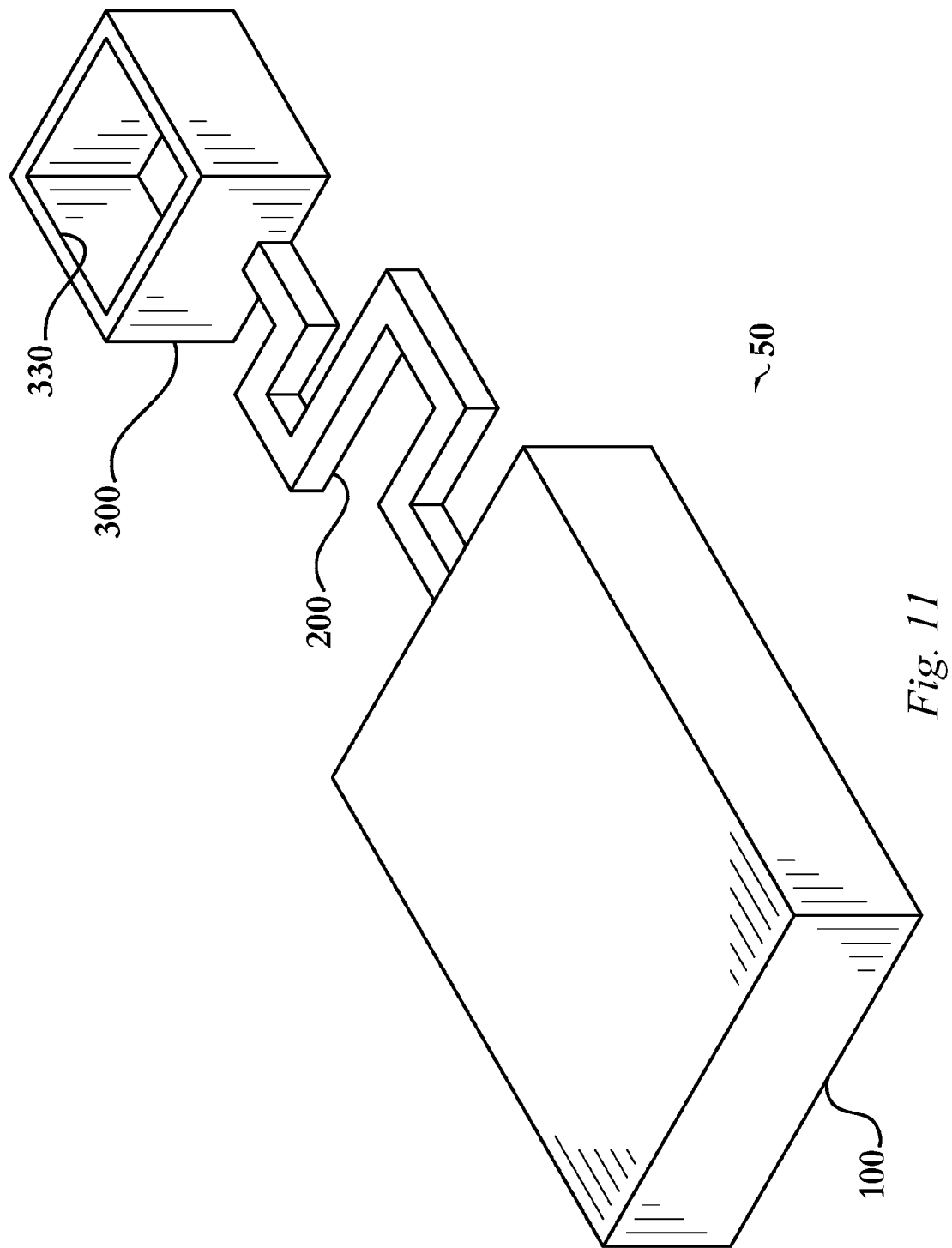
FIG. 11 shows another embodiment of the bioreactor of FIG. 7 in elevated perspective view.
Figure 36:
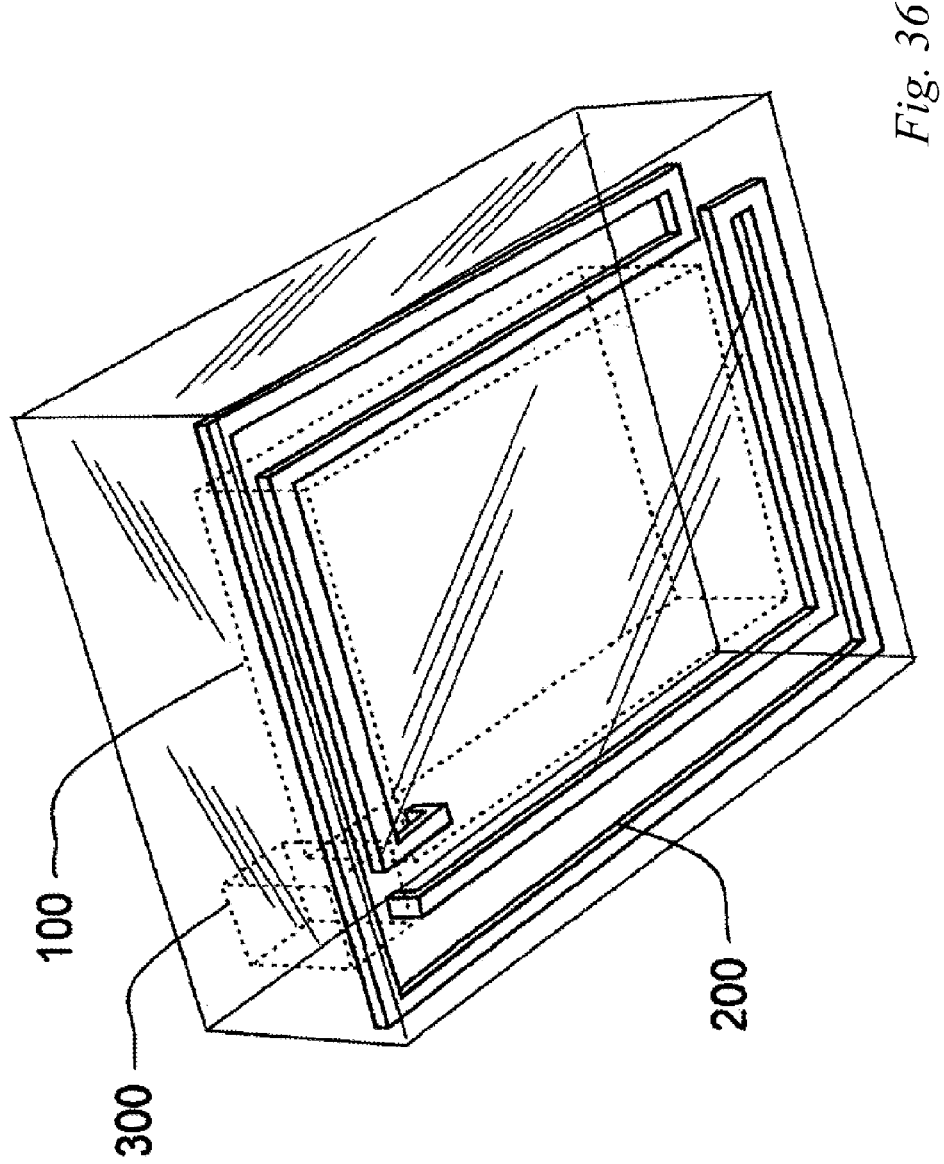
FIG. 36 shows another embodiment of the bioreactor of FIG. 7, in elevated perspective view.

Various substances such as drugs in varying concentrations, nutrients, or other agents, may be introduced into the reagent reservoir (300), which is in fluid communication through the microchannel (200) to the reaction reservoir (100). The reagent reservoir (300) is designed to hold a reagent reservoir volume (320), and the microchannel (200) may be configured with a particular length (230) and cross-sectional area (250), as seen in the preceding embodiment illustrated in FIG. 3. Thus, the delivery by diffusion of a plurality of molecules into and out of the bioreactor (50) may be predetermined and easily effected. The length (230) and cross-sectional area (250) of the microchannel (200) is capable of wide variation, as would be known to one skilled in the art, as long as the basic requirement is met that the microchannel (200) be sized so that there is only laminar flow within the microchannel (200). In several embodiments, a cross-sectional area (250) of less than 4 mm$^2$ performs well. As would be appreciated by one skilled in the art, the rate of diffusion for a given substance, fluid, and temperature is determined by the length (230) and cross-sectional area (250) of the microchannel (200), and is entirely independent of the shape of the microchannel (200), and in particular is independent of any turns in the microchannel (200). Accordingly, and as seen in FIGS. 11 and 36, the microchannel may be configured in a wide array of shapes, including a variety of cross-sectional profiles such as the rectangular and circular profiles seen in the accompanying Figures, in order to accommodate various lengths (230), reagent reservoir volumes (320), and reaction reservoir volumes (120) and other design criteria.

During use, the user fills the microchannel (200), and the reagent reservoir (300) only sufficiently to advance the first fluid to the proximal end of the microchannel (200). At that point, as long is there is a difference in viscosity between the first and second fluid, and unless either the "interfacial tension" between the first fluid and the second is unbalanced in favor of the second, or the microchannel (200) is pressurized above or below the pressure of the reaction reservoir (100), there will be no movement of fluid between the microchannel (200) and the reaction reservoir (100), only diffusion at the interface between the fluids contained in each.

Figure 26:
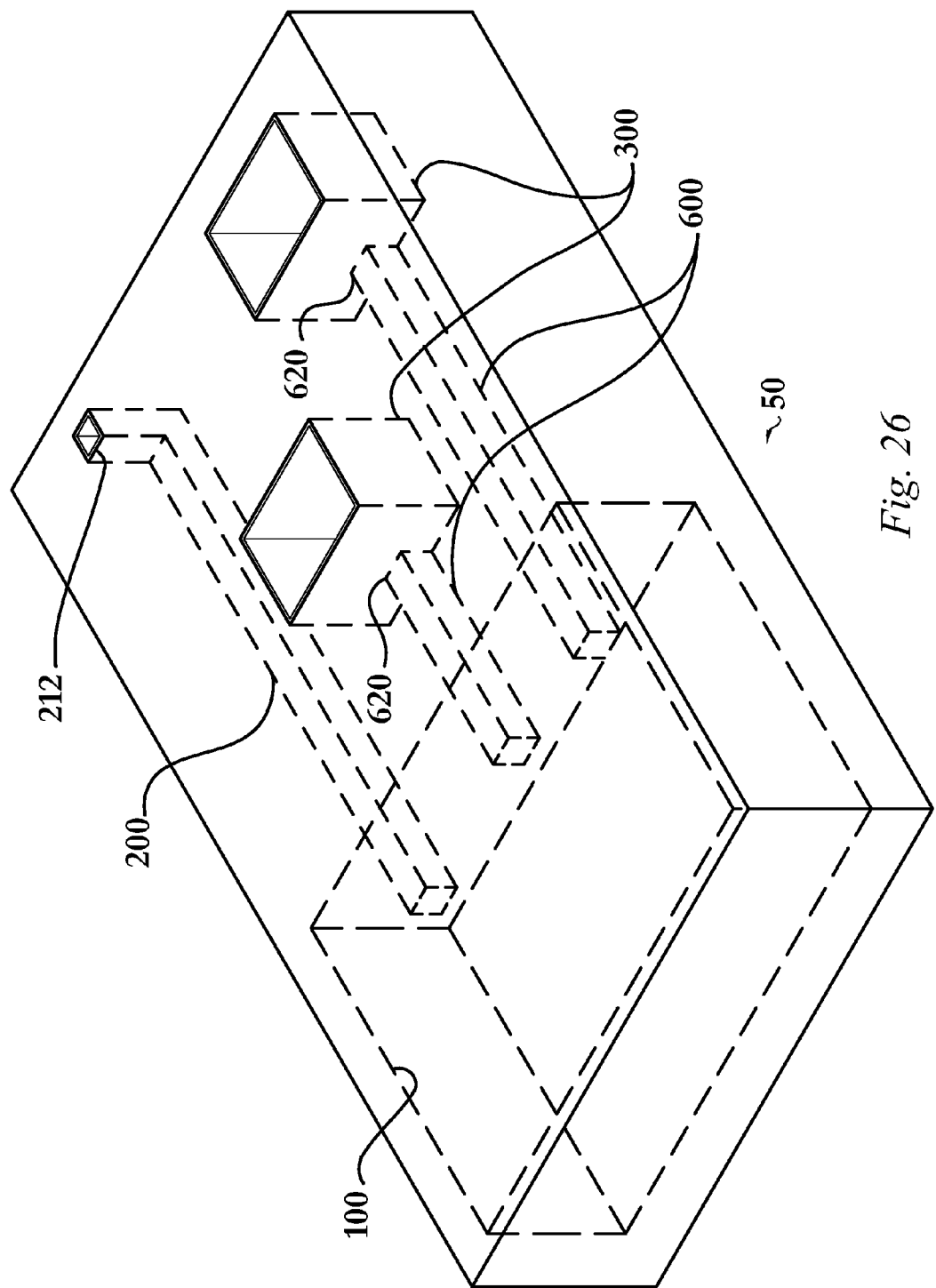
FIG. 26 shows another embodiment of the bioreactor of the instant invention in elevated perspective view.
Figure 31:
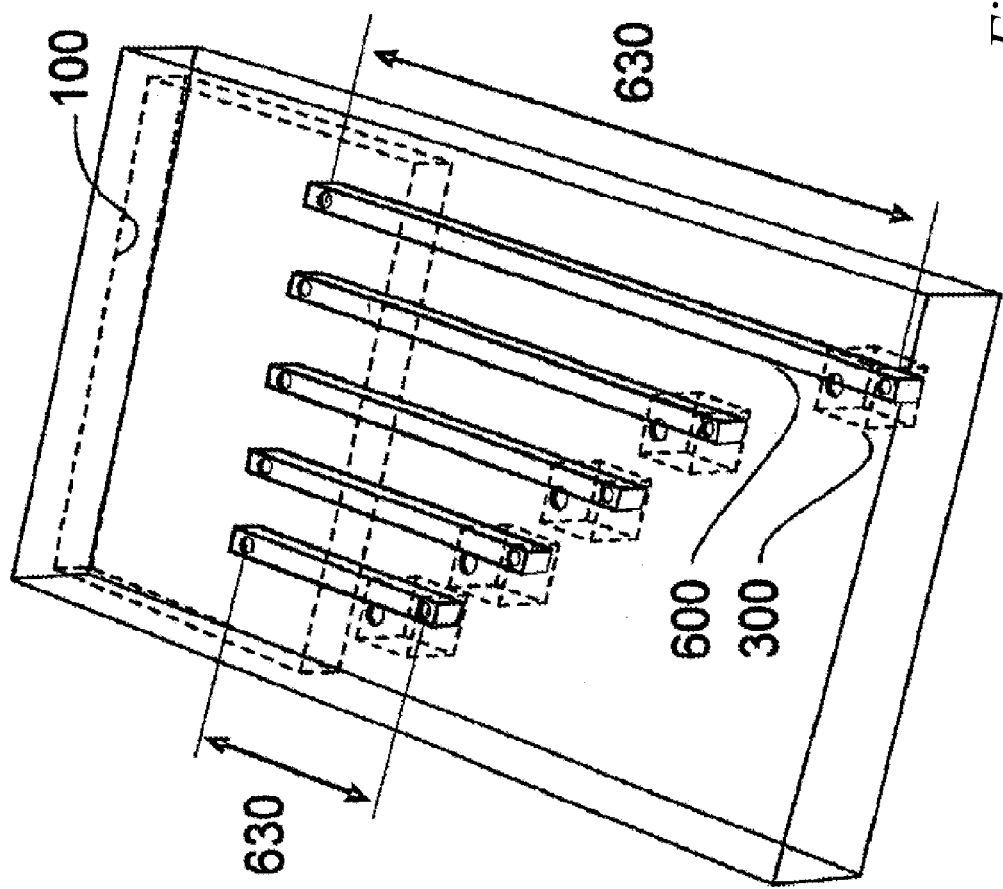
FIG. 31 shows another embodiment of the bioreactor of the instant invention in elevated perspective view.

As would be obvious to one skilled in the art, the diffusion controlling bioreactor (50) may be configured to selectively control the molecular diffusion between a first fluid, a second fluid, and a third fluid. Such multiple fluid handling capacity is seen in the embodiments illustrated in FIGS. 12 and 13, which combine the structures illustrated in FIGS. 3, 4, and 7. A second microchannel (600) may be in fluid communication with the reaction reservoir (100). As with the first microchannel (200), the second microchannel (600) has a proximal end (610) with a proximal end opening (612), and a distal end (620) with a distal end opening (622) as seen in FIG. 14. This second microchannel may further include a reagent reservoir (300) at the distal end (620) of the second microchannel (600) in fluid communication with both the second microchannel (600) and the reaction reservoir (100). The reagent reservoir (300) has at least one reagent reservoir sidewall (310) which defines a reagent reservoir volume (320) and a reagent reservoir opening (330) through which the third fluid enters the reagent reservoir (300). The second microchannel (600) has a length (630), and at least one second microchannel sidewall (640) defining a cross-sectional area. The length (630) and cross-sectional area (650) are selected to obtain a predetermined rate of molecular diffusion between the fluid in the second microchannel (600) and the fluid in the reaction reservoir (100). The second microchannel (600) is configured such when the second microchannel (600) is filled with the third fluid, and the third fluid is a liquid, flow of the third fluid through the second microchannel (600) is laminar. The capillary action of the second microchannel (600) and the third fluid is such that the third fluid does not flow into the reaction reservoir (100) unless the pressure of the third fluid is increased by an external source. The instant invention may be configured to have multiple second microchannels and multiple reagent reservoirs, as illustrated in the embodiments seen in FIGS. 26 and 31.

In the nature of capillary flow, surface tension produces a non-flat liquid surface, called a meniscus, at the end of the microchannel (200). If a fluid tends to wet the inside surface of a capillary such as a microchannel (200), as seen in FIG. 27, the meniscus is concave until capillary action draws the fluid to the open end of the capillary, at which point it becomes convex, as seen in FIG. 28.

In the illustrative example of FIG. 28, a convex meniscus forms at the end of the microchannel 200. Should any hydrophilic material touch the meniscus, or should the meniscus contact a fluid of higher solubility and the "interfacial tension" between the first fluid and the second becomes unbalanced in favor of the second, the surface tension of the meniscus will be broken, and fluid will begin to wick through the capillary microchannel (200), thus potentially defeating the instant invention goal of the prevention of fluid movement through the microchannel (200) and thereby defeating the controlled diffusion of the instant invention. As is well-known in the art, a capillary having a very short sidewall will support only a very slightly convex or concave meniscus. Accordingly, creating a section of very thin sidewall (455) at the proximal end opening (212) of the proximal end (210) of the microchannel (200), as seen in FIGS. 29, 30, 39, and 40, will result in an area wherein the capillary effect of the very thin sidewall (455) at the proximal end (212) will be insufficient to support a meniscus, resulting in a relatively flat interface between a fluid in the microchannel (200) and a fluid in the reaction reservoir (100). In various embodiments, thicknesses in this section of sidewall (455) of between about 0.1 mm and 0.5 mm work well to create this effect.

Figure 40:
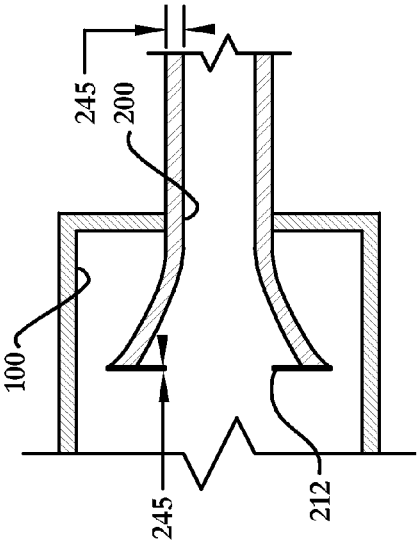
FIG. 40 shows a portion of an embodiment of the bioreactor of the instant invention in cross-sectional view.
Figure 39:
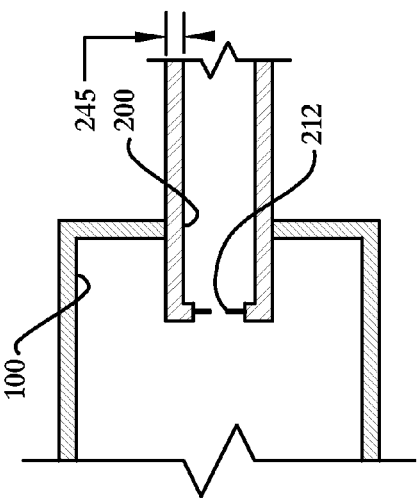
FIG. 39 shows a portion of an embodiment of the bioreactor of the instant invention in cross-sectional view.

As may be seen, by way of examples and not limitation only, one skilled in the art will realize that the area of very thin sidewall (455) at the proximal end opening (212) of the proximal end (210) of the microchannel (200) may be formed in a wide variety of manners, not limited to the embodiments illustrated. In particular, as seen in FIG. 40, it may be seen that the area of very thin sidewall (240) at the proximal end opening (212) of the proximal end (210) of the microchannel (200) does not represent any particular requirements as to diameter of the proximal end opening (212).

Figure 29:
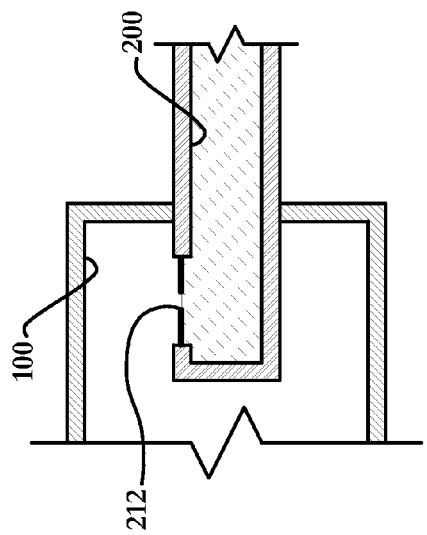
FIG. 29 shows a portion of an embodiment of the bioreactor of the instant invention in cross-sectional view.
Figure 30:
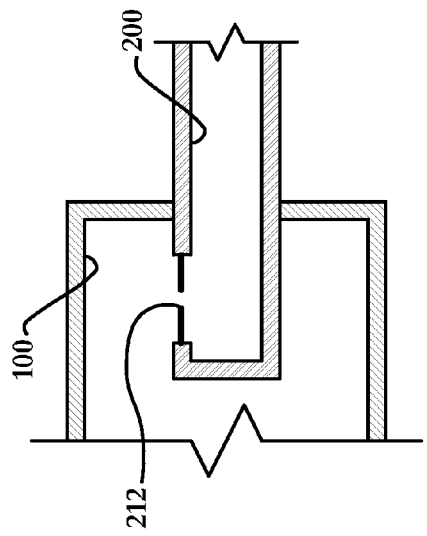
FIG. 30 shows a portion of an embodiment of the bioreactor of the instant invention in cross-sectional view.

To serve the same purpose, the same may be true for a second microchannel (600), where the area of the proximal end opening (612) of the second microchannel (600) may be configured to interpose a section of very thin sidewall (640) at the proximal end opening (612) of the proximal end (610) of the second microchannel (600), analogous to such as seen in FIGS. 29 and 30. As with the first microchannel (200), this will result in an area wherein the capillary effect of the very thin sidewall (640) at the proximal end (612) will be insufficient to support a meniscus, resulting in a relatively flat interface between a fluid in the microchannel (600) and a fluid in the reaction reservoir (100).

In yet another embodiment, seen in FIGS. 14 through 18, the diffusion controlling bioreactor (50) may further include a pressure equalizing vent (400) in fluid communication with the reaction reservoir (100) and a fluidic external environment, wherein the pressure equalizing vent (400) is capable of equalizing the pressure within the reaction reservoir (100) with that of the external environment, as shown in FIG. 15. The pressure equalization vent (400) has a vent microchannel (410) with a distal end (420) with a distal end opening (422) in communication with the external environment. The vent microchannel (410) may further have a length (440), at least one sidewall (450), having a sidewall thickness (455), and defining a cross-sectional area (460), and a proximal end (430) with a proximal end opening (432) in communication with the reaction reservoir (100). The pressure equalizing vent (400) is configured such that when it is filled with a third fluid and the third fluid is a liquid; flow of the third fluid through the pressure equalizing vent (400) is laminar, as with the first microchannel (200) and the second microchannel (600). The capillary action of the pressure equalizing vent (400) and the third fluid is such that the third fluid does not flow out of the distal end opening (422) unless the pressure of the third fluid is increased by an external source.

Figure 7:
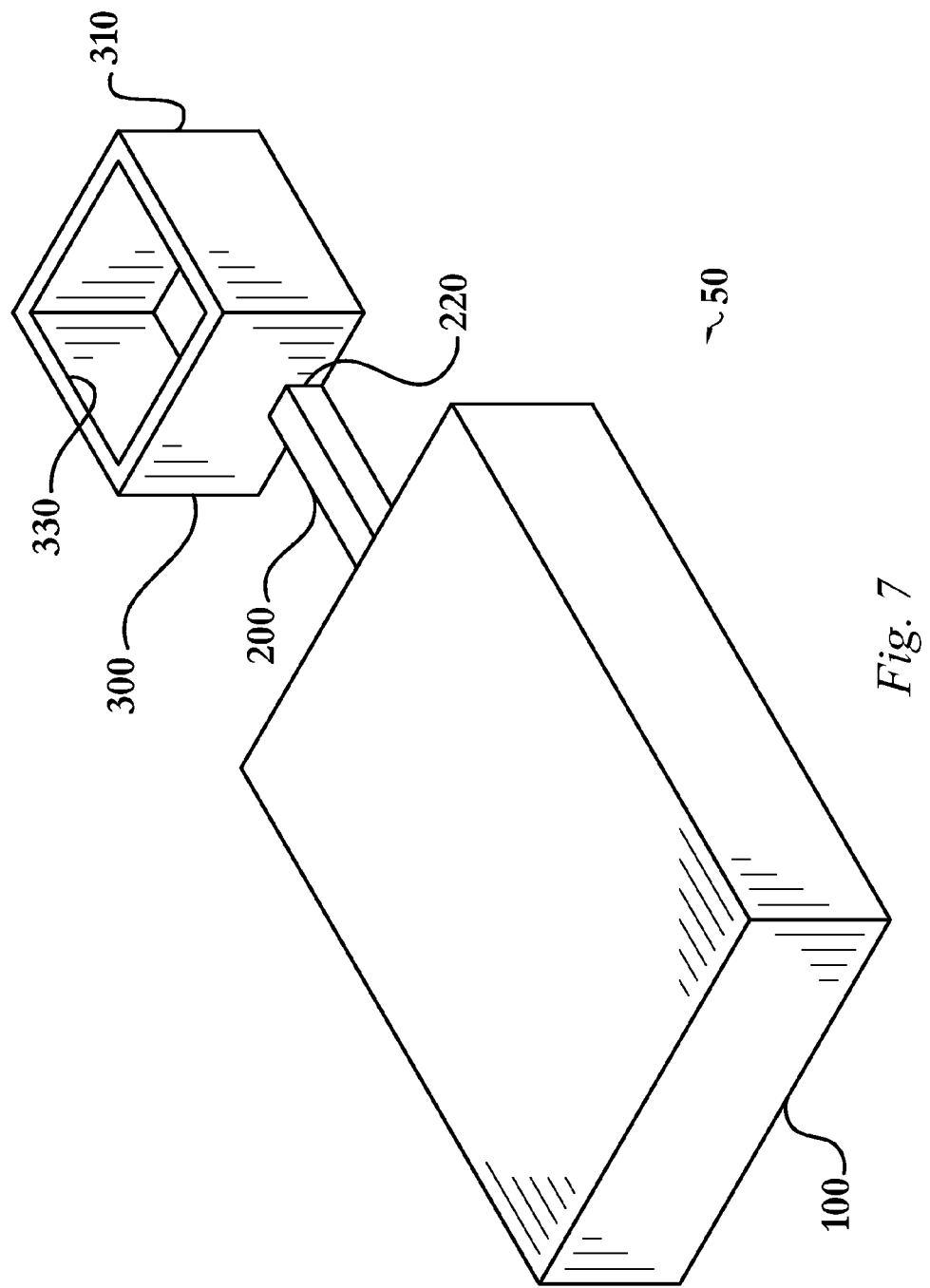
FIG. 7 shows another embodiment of a bioreactor according to the instant invention in elevated perspective view.

An illustrative example of such a pressure equalizing vent (400) is seen in FIGS. 14 through 18. The filling of the reaction reservoir (100) with a second fluid results in a third fluid flowing from the reaction reservoir (100) into the vent microchannel (410) through the proximal end opening (432) of the vent microchannel (410). Examination will reveal that the operative principles regulating the transport of molecules through such a pressure equalizing vent (400) are essentially identical to those of the embodiment utilizing a reagent reservoir (300) and a reaction reservoir (100), as seen in FIG. 7, with the exception that in those embodiments utilizing a pressure equalizing vent (400), the vent microchannel (410) connects the reaction reservoir (100) with an external environment, rather than connecting the reagent reservoir (300) with the reaction reservoir (100), as with the first and second microchannels (200), (600). Thus, there may be passage of gas molecules between the external environment and the reaction reservoir (100), subject to the same controlled diffusion principles as discussed above. Again as applied to the instant invention, the formation of a virtual "seal" by the vent microchannel (410), analogous to the virtual "seal" created by the microchannel (200), may be used to limit the diffusion of gases into and out of the bioreactor (50) to that which takes place across the walls of the bioreactor.

The pressure equalizing vent (400) may include, as seen in FIGS. 17 through 18, at the distal end opening (422), a filter (500) that is hydrophobic and capable of substantially preventing, at normal operating pressures, flow of liquid through the filter (500). The filter (500) may further include an assembly, seen in FIG. 18, of at least 2 layers with a first layer (510) being adapted to prevent the passage of particles having an average size of at least approximately 80 microns, and a second layer (520) being adapted to prevent the passage of particles having an average size of at least approximately 0.2 microns. Such a filter (500) serves two functions, the prevention of the ingress of contaminants greater than the effective filtration size of the filter, i.e., those particles greater than at least approximately 0.2 microns; and the prevention of particle and fluid movement through the hydrophobic filter (500) and into the external environment should the reaction reservoir become somewhat pressurized above the pressure in the pressure equalization vent (400).

Figure 38:
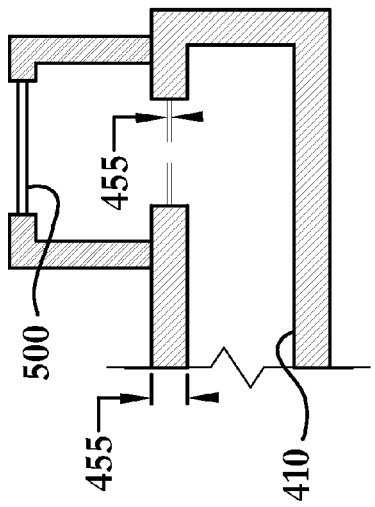
FIG. 38 shows a portion of an embodiment of the bioreactor of the instant invention in cross-sectional view.
Figure 37:
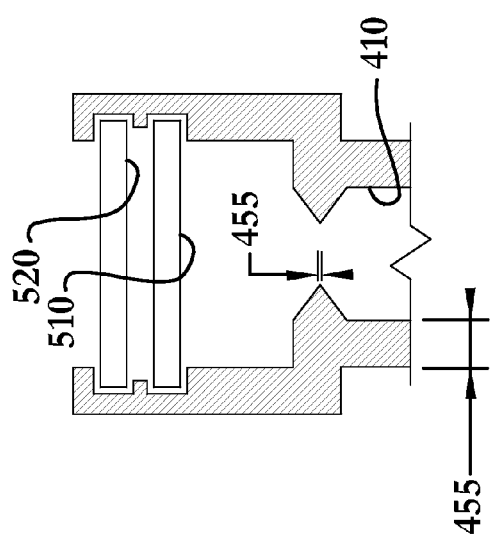
FIG. 37 shows a portion of an embodiment of the bioreactor of the instant invention in cross-sectional view.

A convex meniscus may form at the end of the vent microchannel (400) similar to the meniscus illustrated in FIG. 28, Should this meniscus touch the material of the filter (500), the surface tension of the meniscus will be broken, and fluid will begin to wick through the vent microchannel (410), thus wetting the filter (500) and potentially decreasing the effectiveness of the filter (500). Just as the creation of a section of very thin sidewall (455) at the proximal end opening (212) of the proximal end (210) of the microchannel (200), as seen in FIGS. 29, 30, 39, and 40, will result in an area wherein the capillary effect of the very thin sidewall (455) at the proximal end (212) will be insufficient to support a meniscus at the proximal end (212), an analogous structure, seen in FIGS. 37 and 38; an analogous structure at the distal end (420) of the vent microchannel (410) will result in a relatively flat interface between a fluid in the vent microchannel (410) and a fluid, which may be air, between the distal end (420) and the filter (500).

The flatter meniscus is less likely to extend beyond the distal end opening (422) of the vent microchannel (400), and therefore the fluid in the vent microchannel (410) is less likely to contact the filter (500). In various embodiments, thicknesses in this section of sidewall (455) of between about 0.1 mm and 0.5 mm work well to create this effect.

Figure 19:
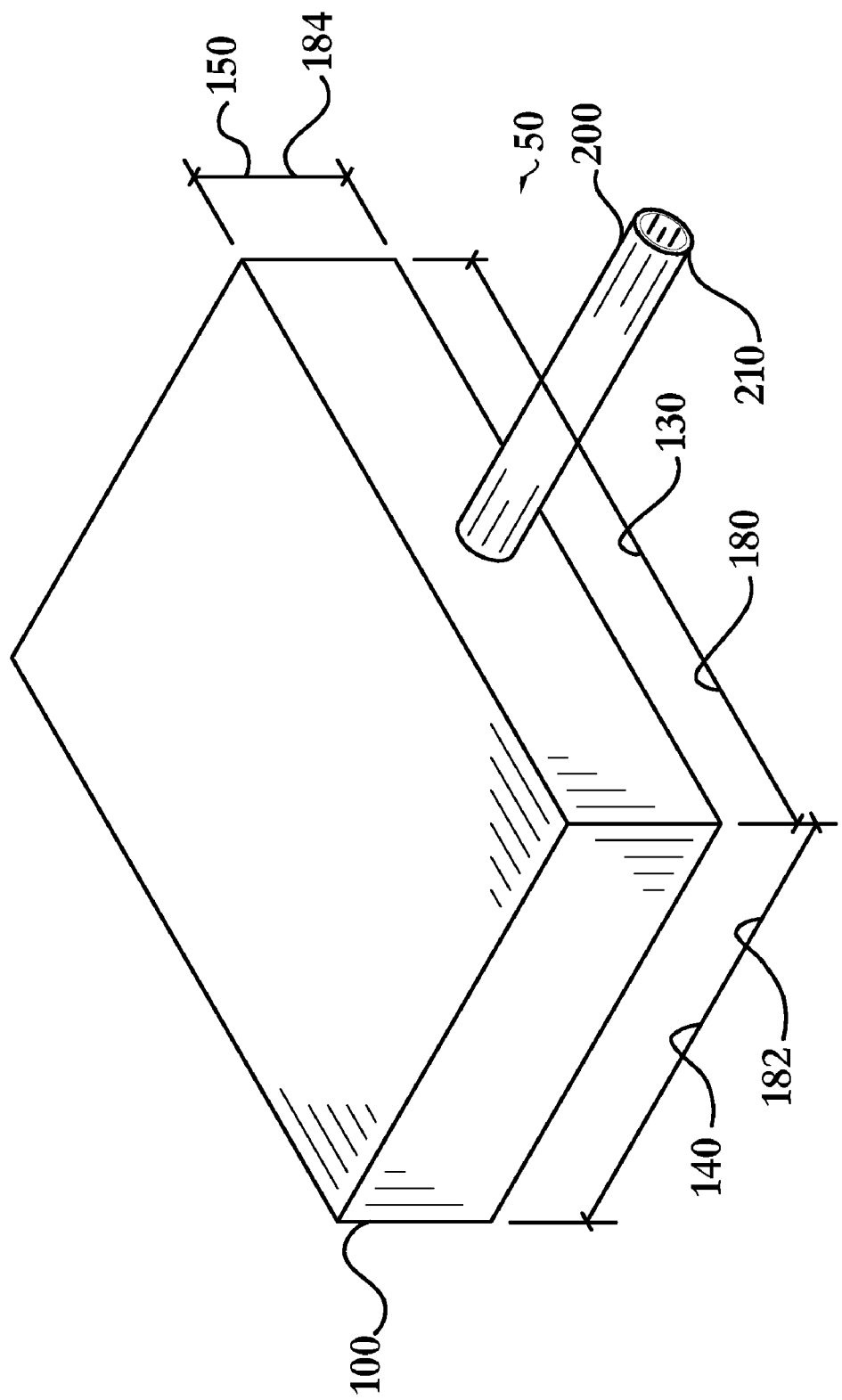
FIG. 19 shows another embodiment of the bioreactor of FIG. 2 in elevated perspective view.
Figure 20:
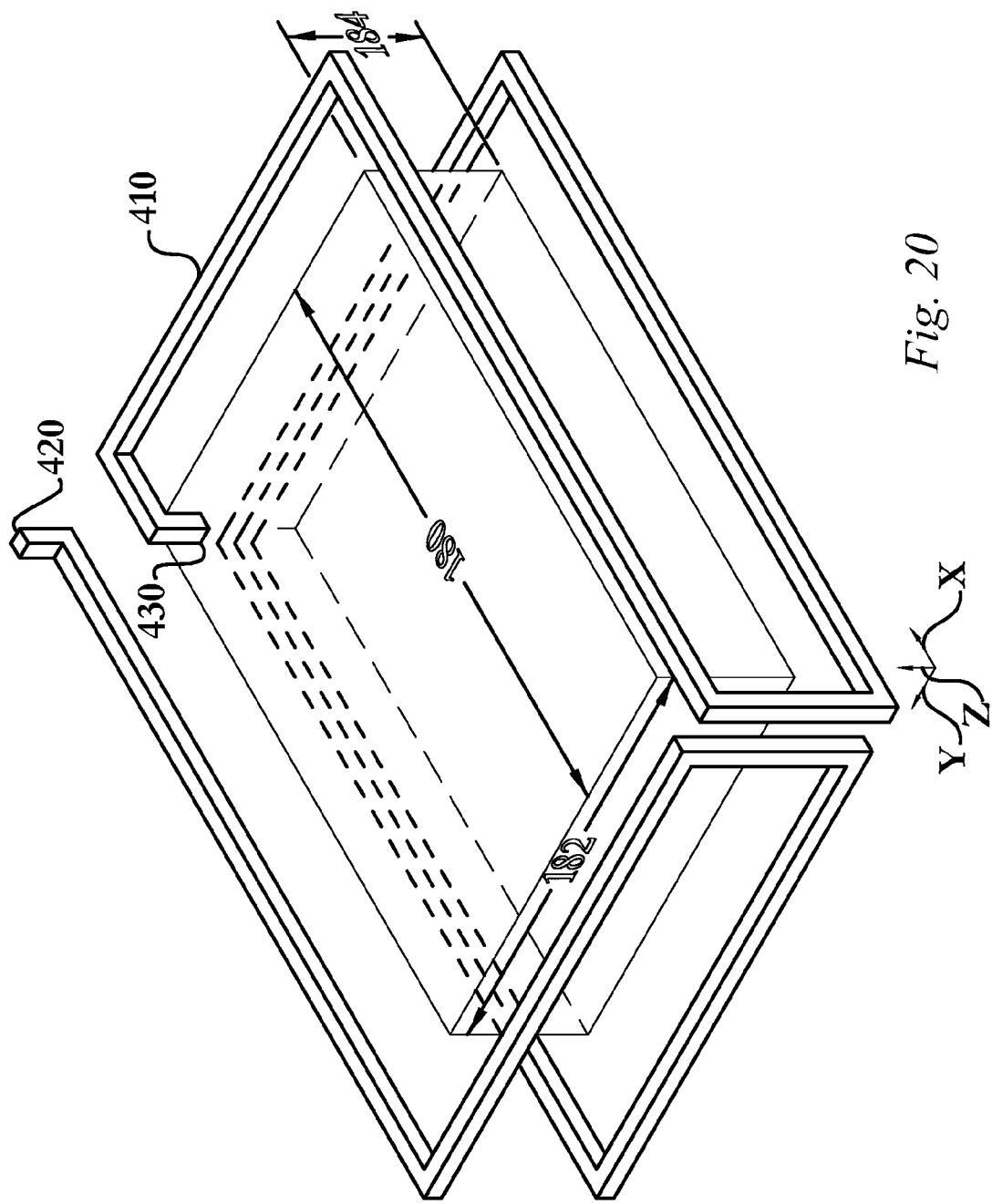
FIG. 20 shows another embodiment of the bioreactor of FIG. 19 in elevated perspective view.
Figure 25:
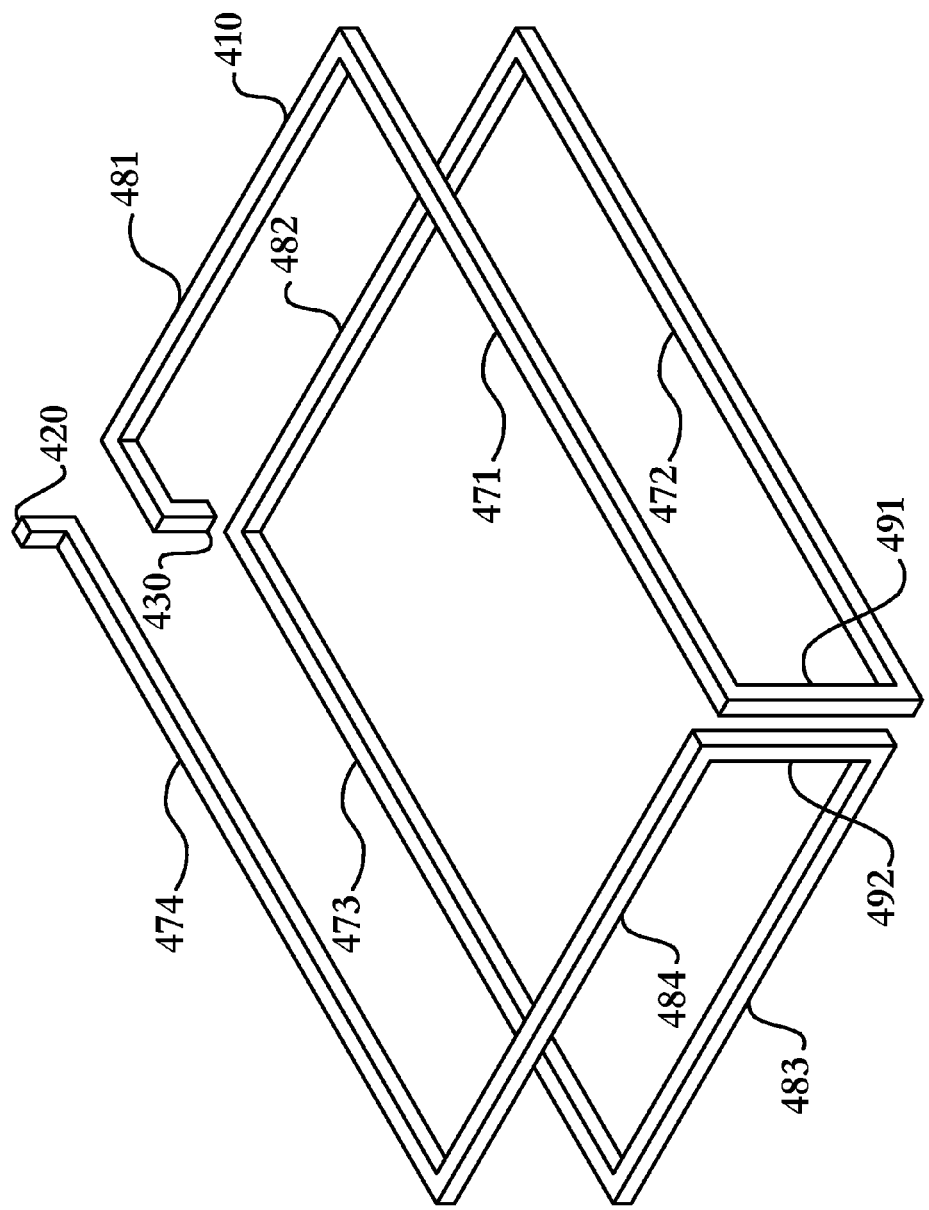
FIG. 25 shows a portion of the embodiment of FIG. 20 of the bioreactor of the instant invention in elevated perspective view.

The pressure equalizing vent (400) may have a structure configured to minimize the chances of fluid leakage from the bioreactor (50), seen in FIGS. 20 and 25, even if the bioreactor (50) is turned in various directions. In such an embodiment, the reaction reservoir (100) has a maximum first dimension in a primary axis (130), a maximum second dimension in a secondary axis (140), and a maximum third dimension in a tertiary axis (150), seen in FIG. 19. Further, seen in FIG. 20, in such a design, the pressure equalizing vent (400) includes a continuous vent microchannel (410) configured exterior to the reaction reservoir (100). Such a vent microchannel (410) would include at least one component in the primary axis X with a magnitude greater than the maximum first dimension (130), at least one component in the secondary axis Y with a magnitude greater than the maximum second dimension (140), and at least one component in the tertiary axis Z with a magnitude greater than the maximum third dimension (150), as seen in FIG. 19.

In a preferred embodiment, seen in FIGS. 21 and 24, the reaction reservoir is a hexahedron having a first longitudinal surface (162), a second longitudinal surface (164), a first lateral surface (166), a second lateral surface (168), a top surface (170), and a bottom surface (172), thereby defining a reaction reservoir length (180), width (182), and depth (184), as seen in FIG. 20. In such an embodiment, as seen in FIG. 25, the continuous vent microchannel (410) has four sections (471), (472), (473), (474) substantially parallel to the length (180) and greater in magnitude than the length (180); four sections (481), (482), (483), (484) substantially parallel to the width (182) and greater in magnitude than the width (182); and two sections (491), (492) substantially parallel to the depth (184) and greater in magnitude than the depth (184).

Examination of such an embodiment shows that should the bioreactor (50) be rotated though one or more dimensions of space, the configuration is such that the vent microchannel (410) would include at least one component of the sections in the primary axis X with a magnitude greater than the maximum first dimension (130), at least one component of the sections in the secondary axis Y with a magnitude greater than the maximum second dimension (140), and at least one component of the sections in the tertiary axis Z with a magnitude greater than the maximum third dimension (150). This results in at least a portion of at least one section (471), (472), (474), (474), (481), (482), (483), (484), (491), (492) lying above the fluid level in the bioreactor (50) at all times. As such, during rotation, a significant portion of the fluid in the vent microchannel (410) will drain back into the reaction reservoir (100), while a portion will advance into the adjoining section (471), (472), (474), (474), (481), (482), (483), (484), (491), (492) of the vent microchannel (410). This drain and advance process will be repeated with each turn in any dimension of the bioreactor (50), such that only a concerted effort to rotate the bioreactor (50) through sequential turns in more than one dimension, designed to advance the fluid through the vent microchannel (410), will result in a significant amount of fluid reaching the filter (500).

The tendency for the fluid in one section of the vent microchannel (410) to drain back into the reaction reservoir (100) during rotation of the bioreactor (50) also acts to minimize pressure build up at the distal end opening (422) of the vent microchannel (410) due to a static column of fluid, as the weight of the fluid in a draining section tends to counteract, and thereby pull back, against the weight of any fluid advancing in the vent microchannel (410). The minimization of pressure at the distal end opening (422) of the vent microchannel therefore tends to minimize expulsion of fluid at the distal end opening (422) of the vent microchannel (410), should any fluid reach the distal end opening (422), and thereby to minimize the chances of fluid contamination of the filter (500).

In other preferred embodiments, the bioreactor (50) may be configured with a plurality of reagent reservoirs (300), each at the distal end (620) of a second microchannel (600) that is in fluid communication with both the second microchannel (600) and the reaction reservoir (100). In such an embodiment, each reagent reservoir (300) may be in fluid communication with a second microchannel (600) having different second microchannel lengths (630), and/or cross sectional areas (650) from the other second microchannels (600). This, as seen in illustrative embodiments in FIGS. 26 and 31, enables multiple simultaneous controlled diffusion processes involving different substances to take place coincidentally, but at different rates. Such multiple arrangements of reagent reservoirs (300) in fluid communication through second microchannels (600) to the reaction reservoir (100) is ideal, as would be appreciated by one skilled in the art, for testing or controlling the effects of diffusion of various drugs, nutrients, or other substances, into the process contained in the bioreactor (50). Additionally, the very slow rates of diffusion that may be achieved by the bioreactor (50) of the instant invention make it ideal for the transport of very small quantities of substances into the bioreactor (50) in a very stable and accurate manner over long periods of time.

Figure 32:
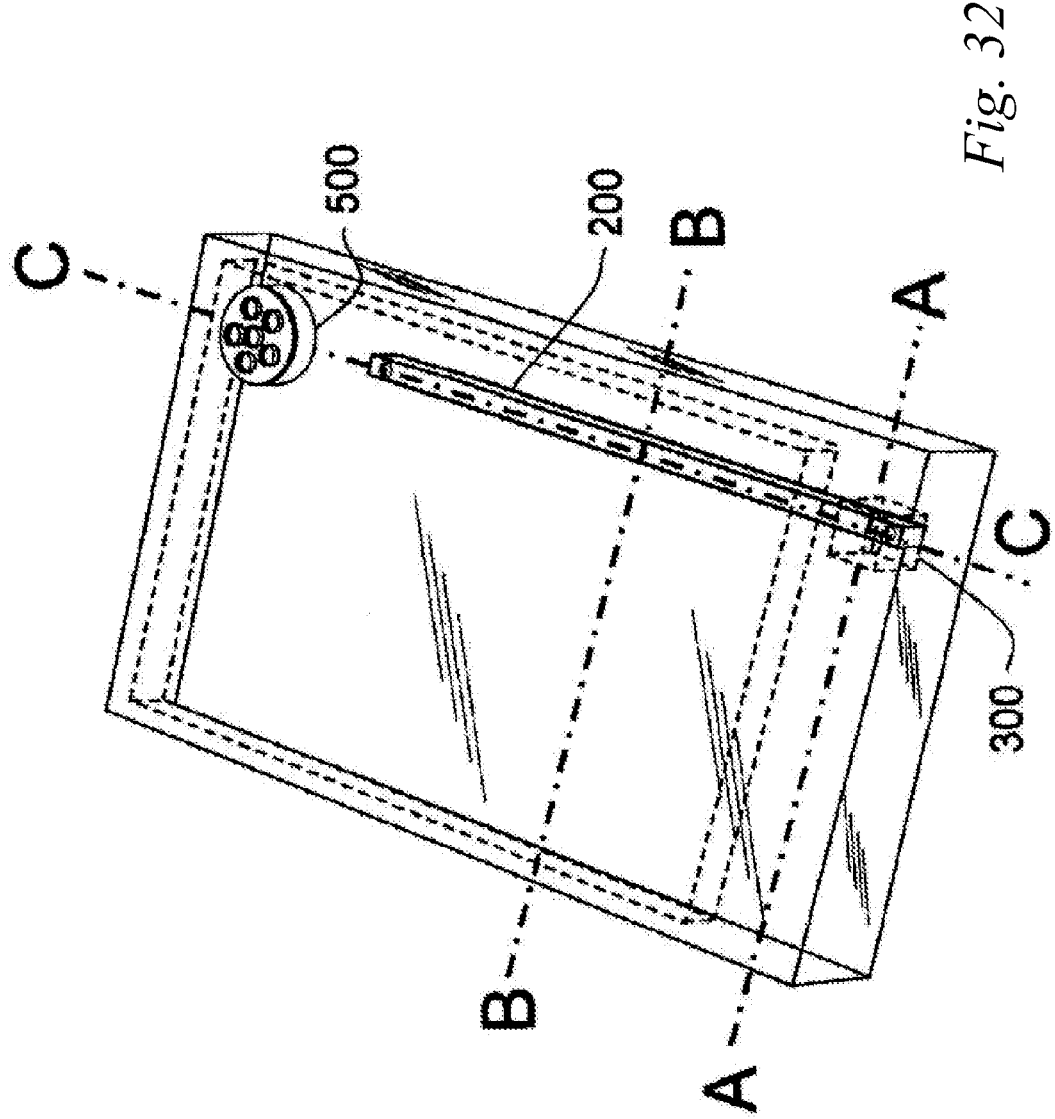
FIG. 32 shows another embodiment of the bioreactor of the instant invention in elevated perspective view.

An illustrative embodiment of the instant invention is seen in FIGS. 31-35. In this embodiment, the reaction reservoir (100), first microchannel (200) and filter (500) are formed as part of an integral structure, for strength and ease of handling, as seen in FIG. 32. In FIG. 33, a penetrable elastomeric septum (333) closes the reagent reservoir (300) at the distal end (220) of the microchannel. As seen in FIG. 34, the microchannel (200) runs within the integral structure, and inferior to the reaction reservoir (100). In this particular illustrative embodiment, in which the reaction reservoir (100) may be vented as shown, viewed in cross-section in FIG. 35, the relationship between the reaction reservoir (100), a microchannel (200), and a filter (500) may be visualized.

In yet another series of embodiments, a bioreactor (1010), as seen well in FIGS. 41-64, may include a plurality of fluid-filled structures having three-dimensional relationships among the structures defined in terms of an orthogonally related bioreactor (1010) x-axis, y-axis, and z-axis. As seen well in FIGS. 41 and 42, the structures are bounded within an external frame (1012), and may, in one illustrative embodiment, further include, at least a first microchannel (1200) having a first microchannel distal end (1210) and a first microchannel distal end opening (1212), at least a first microchannel medial sidewall (1222) and at least a first microchannel lateral sidewall (1224). The first microchannel (1200) may have a first microchannel cross-sectional area, and a first microchannel proximal end (1240).

Throughout this specification, the term "medial" shall be used to describe aspects closer to the central portion of the bioreactor (1010), while the term "lateral" shall be used to describe aspects closer to the edges of the bioreactor (1010). Also, throughout this specification, the term "proximal" shall be used to describe aspects closest to the reaction reservoir (1100) along a shortest fluid path, while the term "distal" shall be used to describe aspects farthest from the reaction reservoir (1100) along a shortest fluid path. Therefore, by way of example, in the normal filling of the bioreactor (1010), contents would enter at the first microchannel distal end (1210) and first microchannel distal end opening (1212) and would exit into the reaction reservoir (1100) at the first microchannel proximal end (1240).

With reference to FIGS. 43-49, a reaction reservoir (1100) may have at least one reaction reservoir sidewall (1120) and a reaction reservoir volume, in fluid communication with the first microchannel proximal end (1240) through a first microchannel proximal end-reaction reservoir fenestration (1242). Such a first microchannel proximal end-reaction reservoir fenestration (1242) may include at least one first microchannel proximal end-reaction reservoir fenestration height (1244) and at least one first microchannel proximal end-reaction reservoir fenestration width (1246) defining at least one first microchannel proximal end-reaction reservoir fenestration cross-sectional area, as seen in detail in FIG. 62. Although the first microchannel proximal end-reaction reservoir fenestration (1242) is shown in the drawings as having a rectangular geometry, other geometries are contemplated, such as circular, elliptical, oval, and square, just to name a few.

Figure 41:
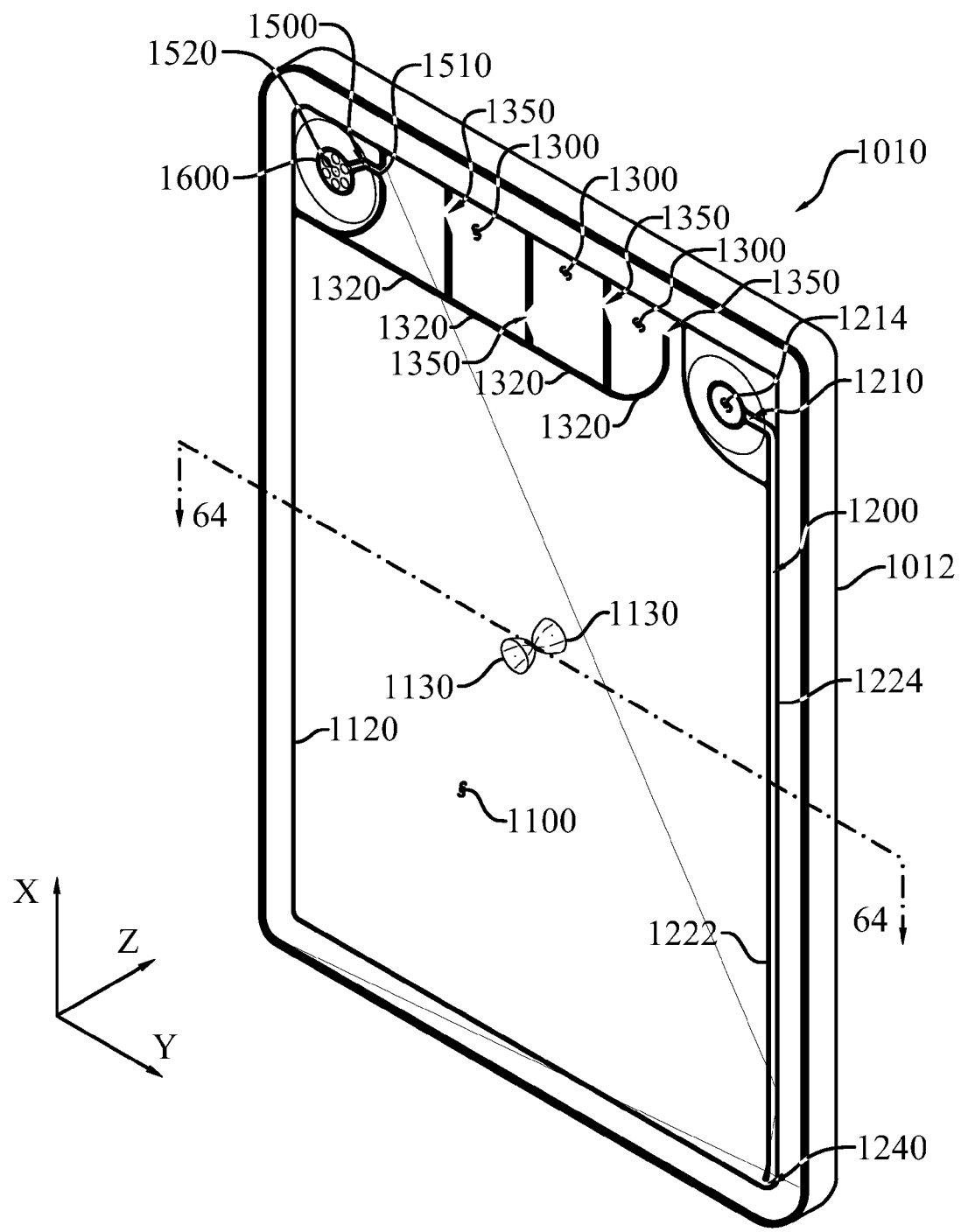
FIG. 41 shows an elevated perspective view of an embodiment of the bioreactor of the instant invention in cross-sectional view.
Figure 42:
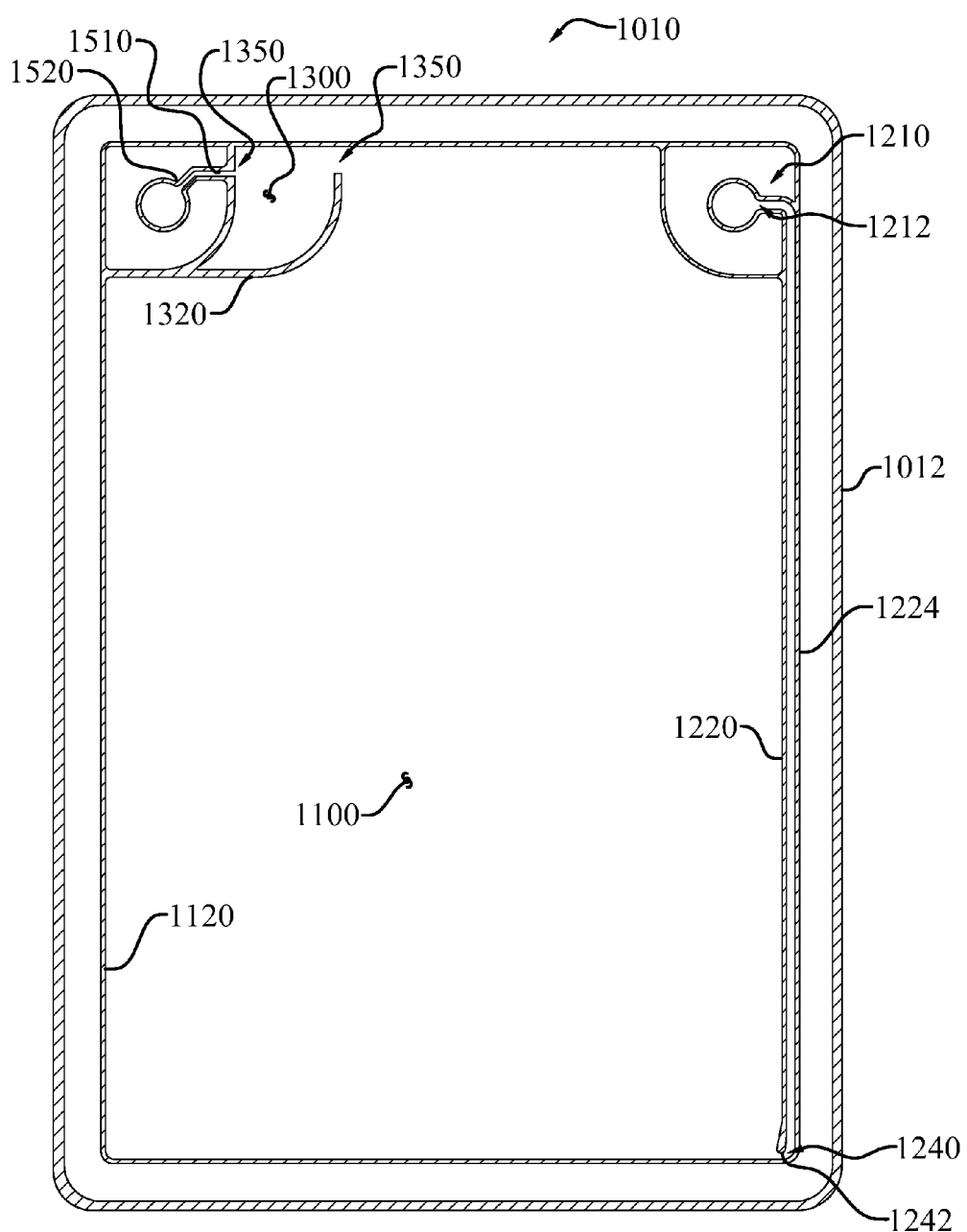
FIG. 42 shows a view of an embodiment of the bioreactor of the instant invention in cross-sectional view.
Figure 43:
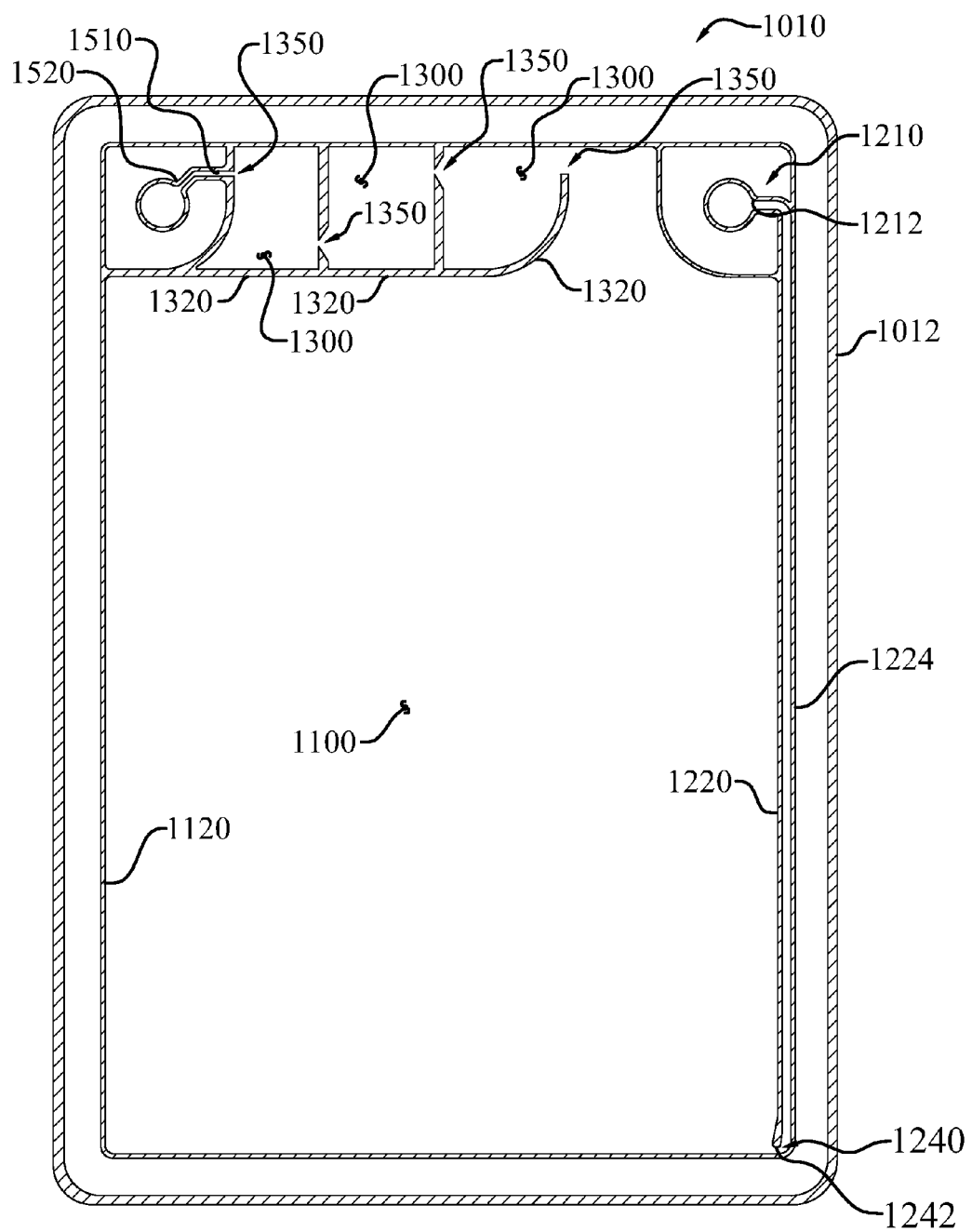
FIG. 43 shows a view of an embodiment of the bioreactor of the instant invention in cross-sectional view.
Figure 44:
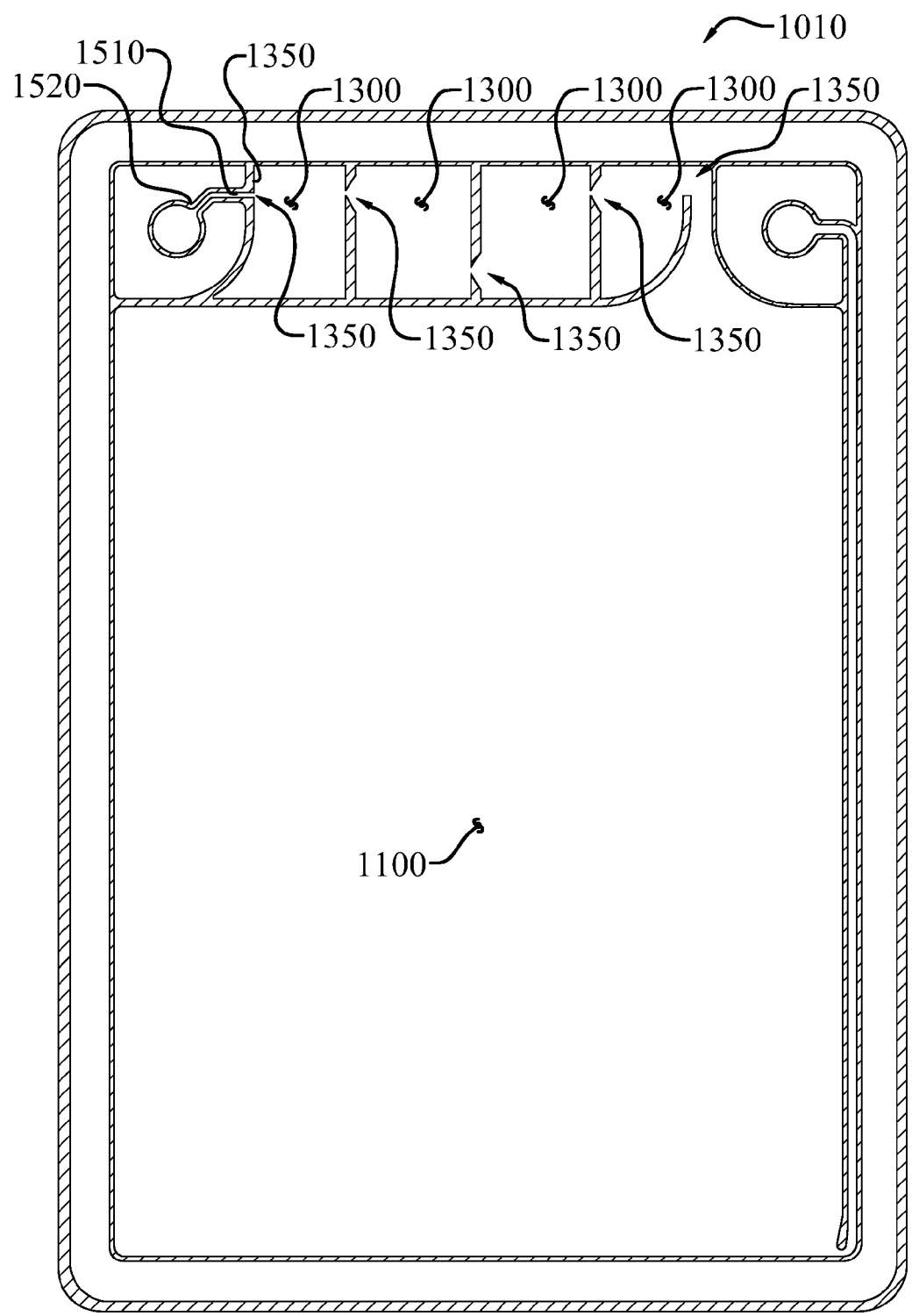
FIG. 44 shows a view of an embodiment of the bioreactor of the instant invention in cross-sectional view.
Figure 45:
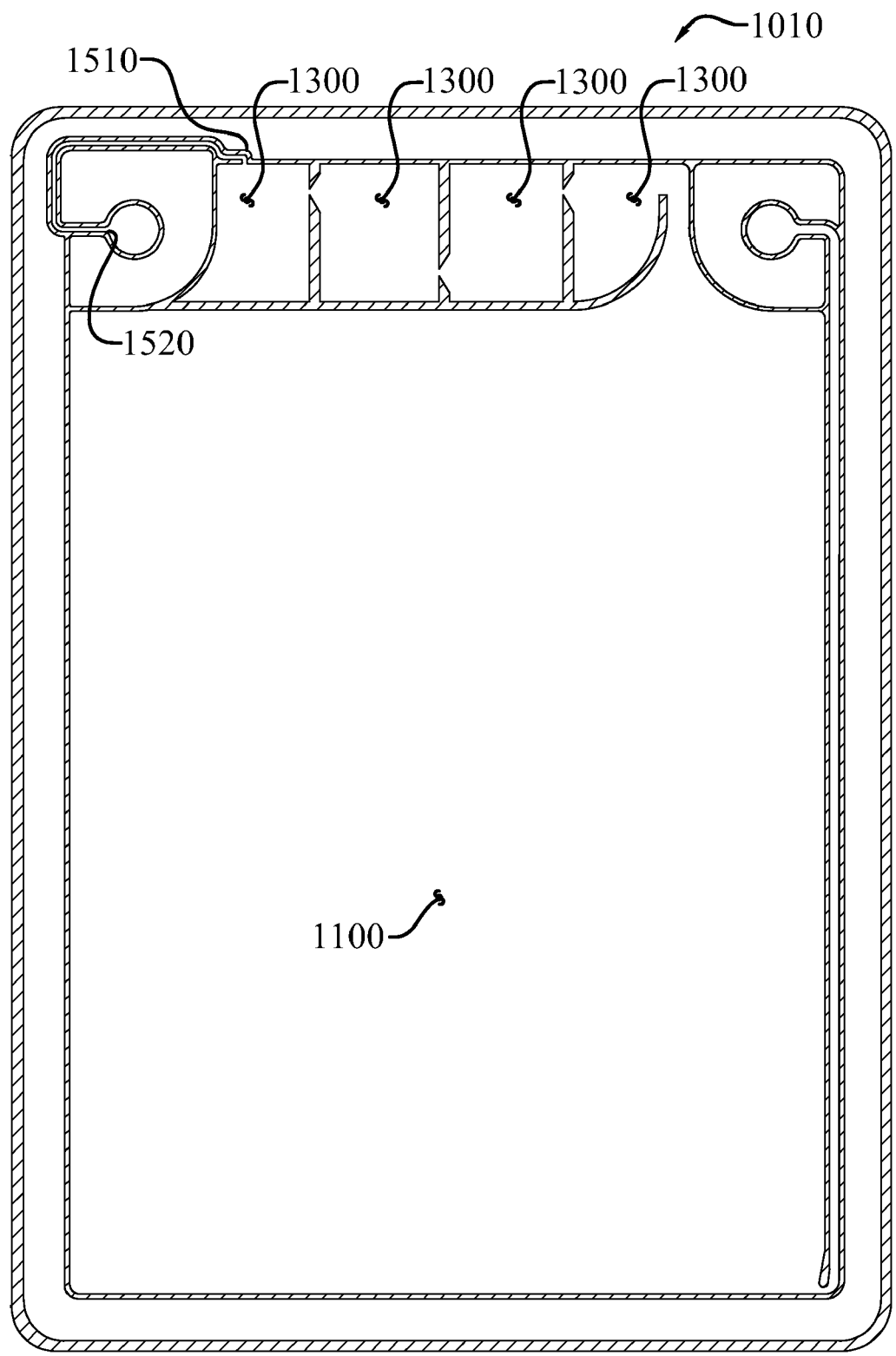
FIG. 45 shows a view of an embodiment of the bioreactor of the instant invention in cross-sectional view.
Figure 46:
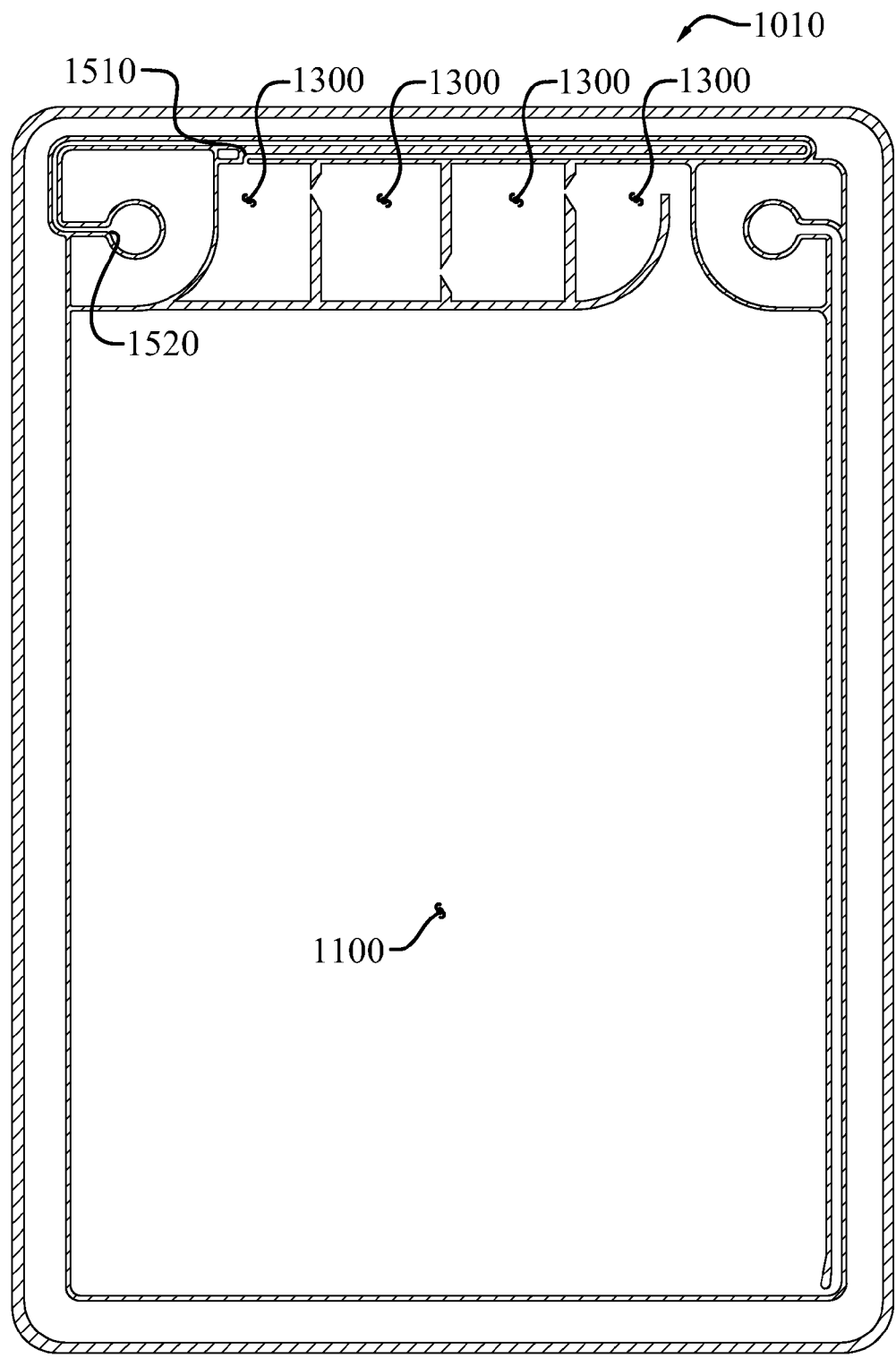
FIG. 46 shows a view of an embodiment of the bioreactor of the instant invention in cross-sectional view.
Figure 47:
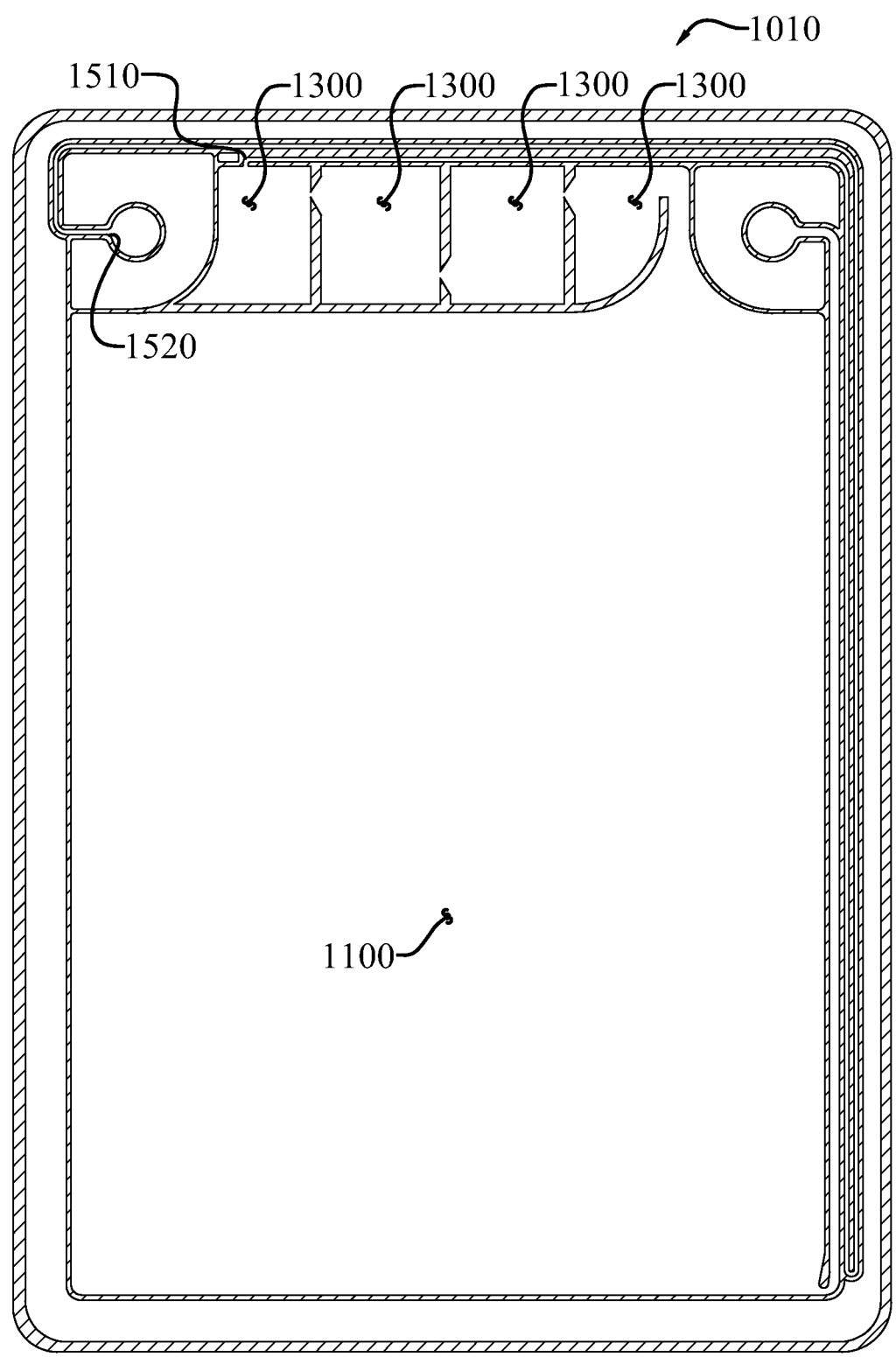
FIG. 47 shows a view of an embodiment of the bioreactor of the instant invention in cross-sectional view.
Figure 48:
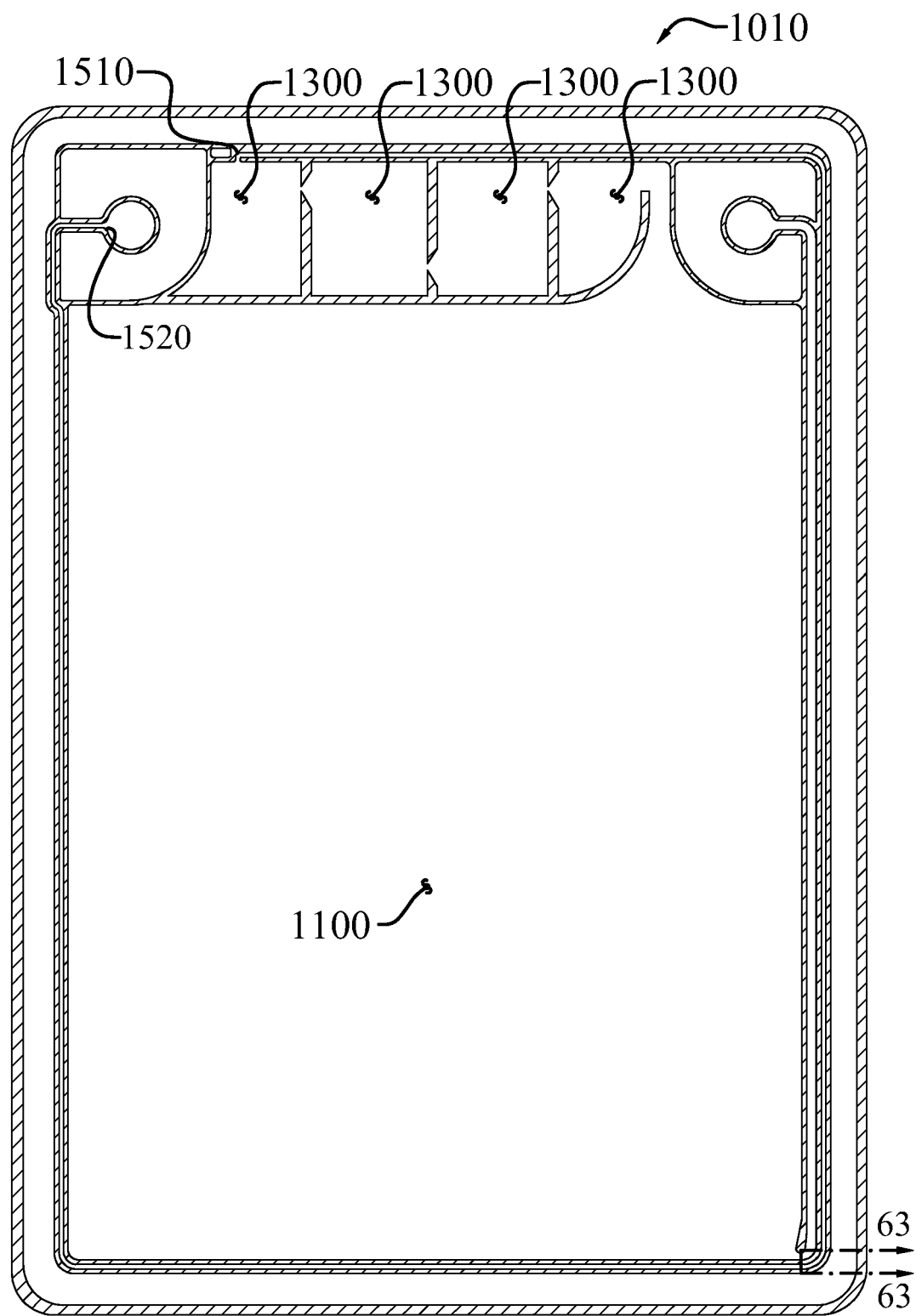
FIG. 48 shows a view of an embodiment of the bioreactor of the instant invention in cross-sectional view.
Figure 49:
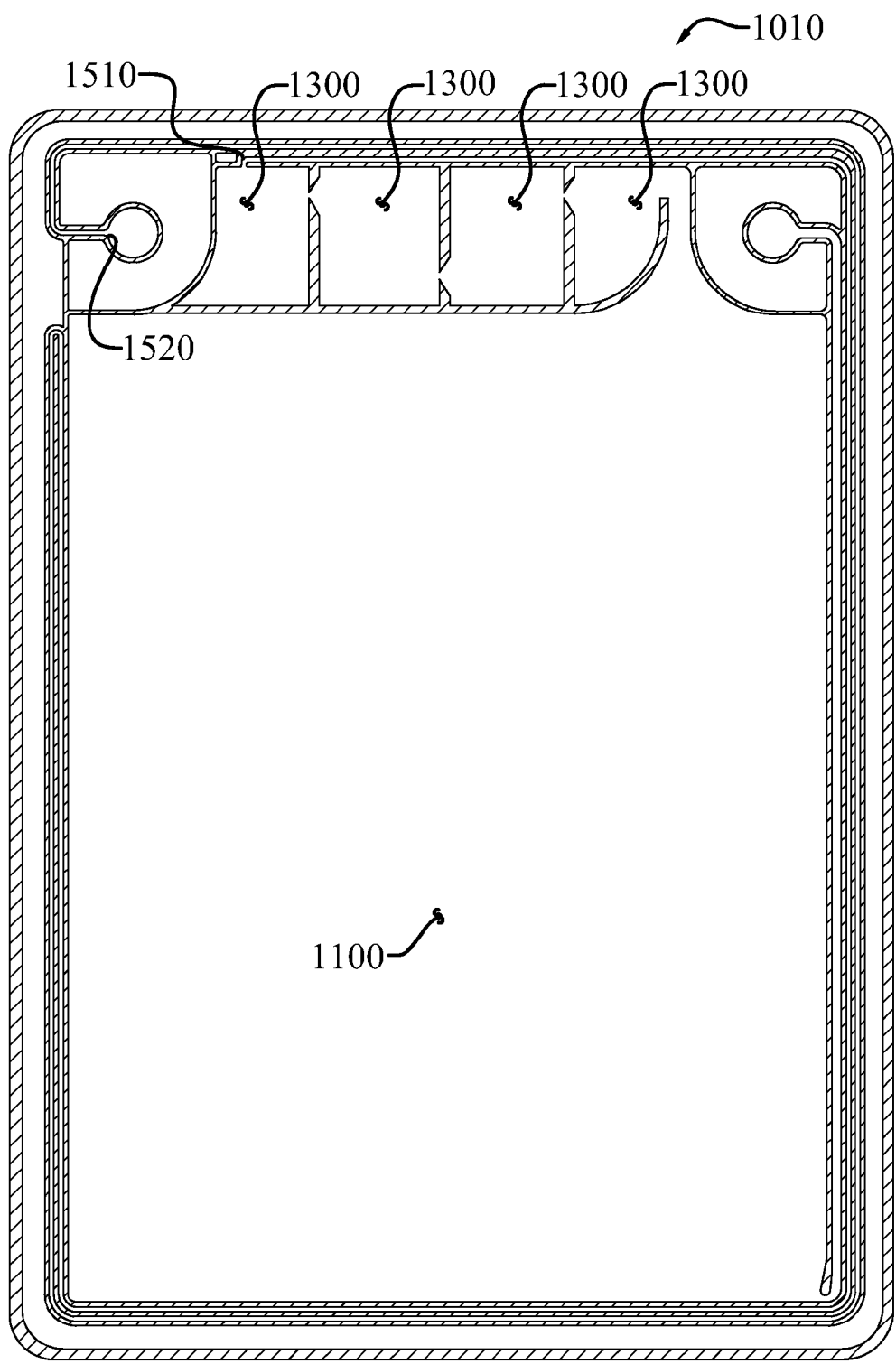
FIG. 49 shows a view of an embodiment of the bioreactor of the instant invention in cross-sectional view.
Figure 50:
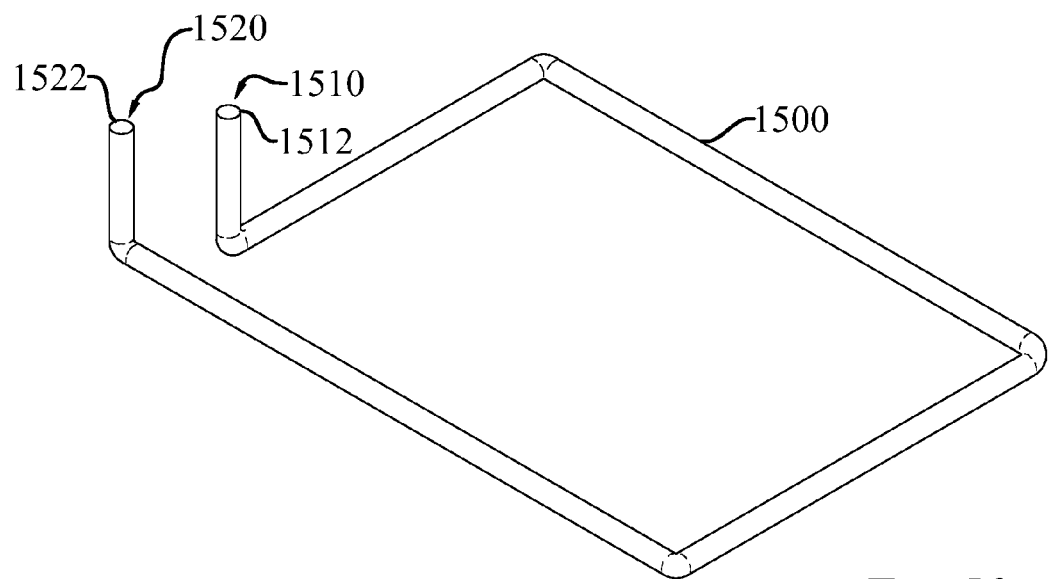
FIG. 50 shows a detail view of an embodiment of the bioreactor of the instant invention, and in particular of an embodiment of the second microchannel, in elevated perspective view.
Figure 51:
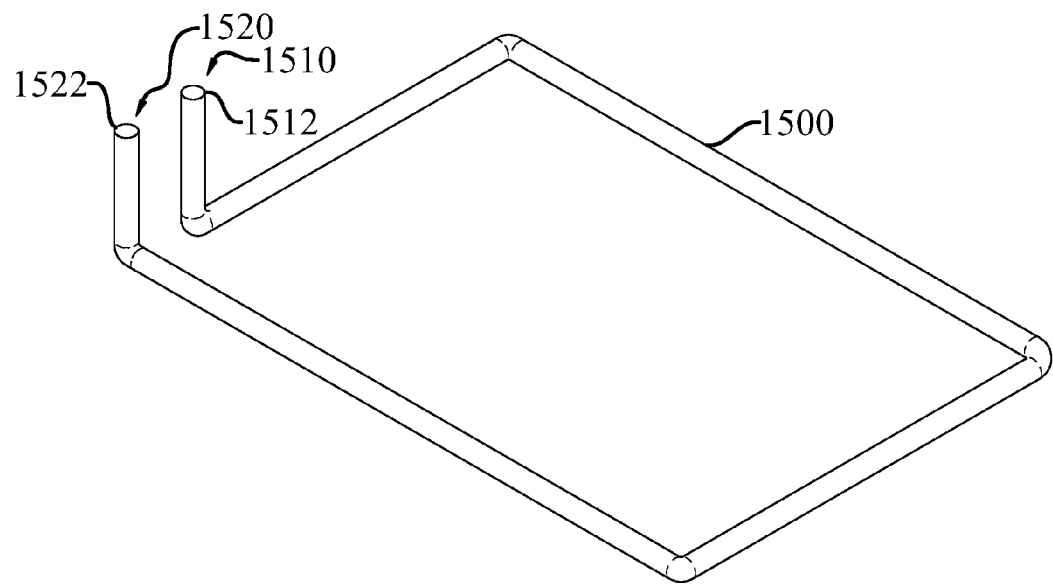
FIG. 51 shows a detail view of an embodiment of the bioreactor of the instant invention, and in particular of an embodiment of the second microchannel, in elevated perspective view.
Figure 52:
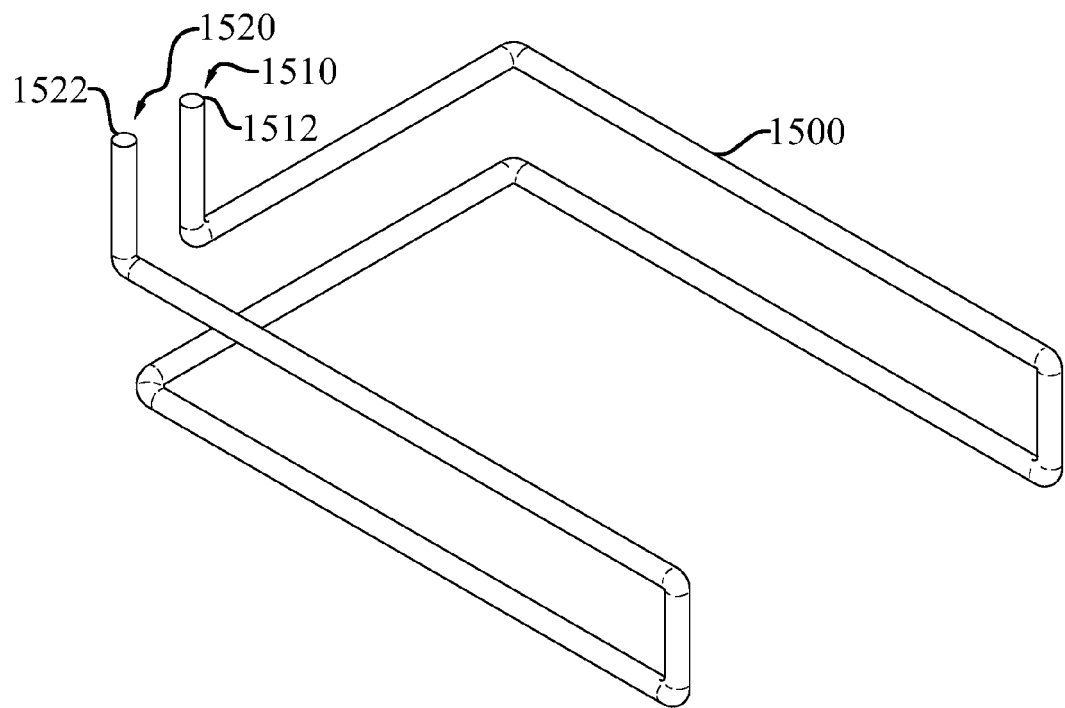
FIG. 52 shows a detail view of an embodiment of the bioreactor of the instant invention, and in particular of an embodiment of the second microchannel, in elevated perspective view.
Figure 53:
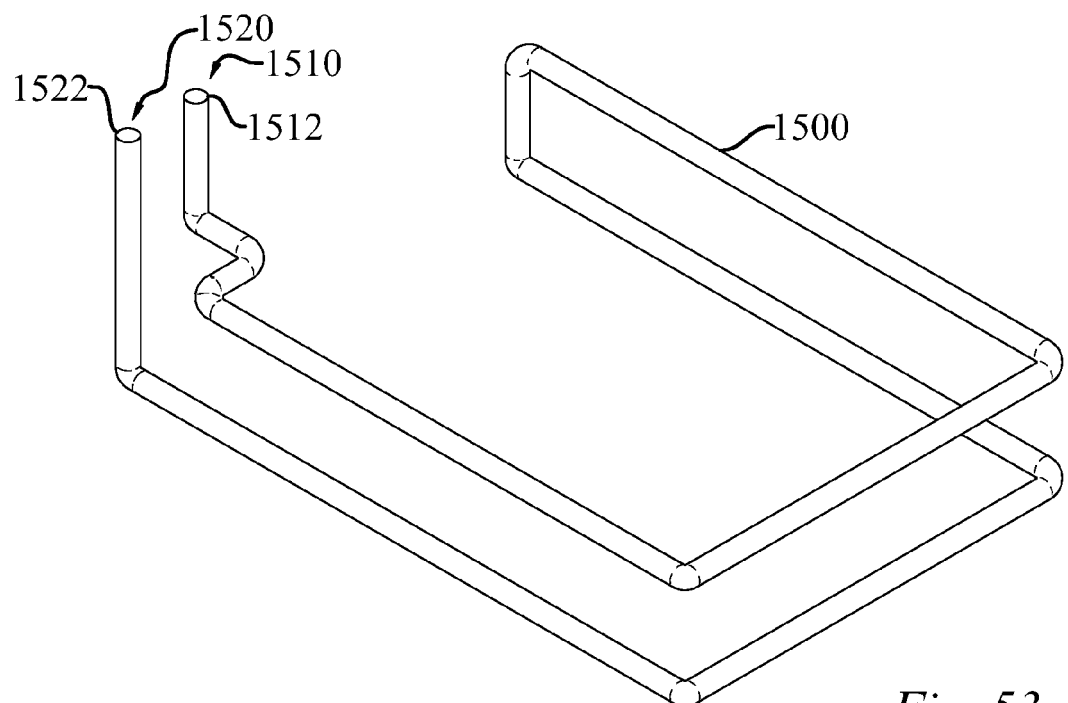
FIG. 53 shows a detail view of an embodiment of the bioreactor of the instant invention, and in particular of an embodiment of the second microchannel, in elevated perspective view.

In one embodiment, seen well in FIGS. 41 and 42, at least one diffusion control chamber (1300) may include at least one first diffusion control chamber sidewall (1320) and having a first diffusion control chamber volume in fluid communication with the reaction reservoir (1100) through at least a first diffusion control chamber fluid flow control port (1350). There may be at least a second microchannel (1500) having a second microchannel proximal end (1510), a second microchannel distal end (1520), a second microchannel length and a second microchannel cross-sectional area. Such a second microchannel (1500) may be in fluid communication with the at least one diffusion control chamber (1300) through at least a second diffusion control chamber fluid flow control port (1350) and in at least reversible fluid communication with an ambient atmosphere through the second microchannel proximal end (1520).

In a variety of additional embodiments, seen by way of illustration only and not limitation in FIGS. 43-49, the previously described bioreactor (1010) may include more than one diffusion control chamber (1300) in fluid communication with the first fluid diffusion control chamber (1300). It is specifically intended by this specification that there be no absolute upper limit on the number of diffusion control chambers (1300).

In another series of embodiments, as seen by way of example only and not limitation in FIGS. 43-49, the length of the second microchannel (1500), which may be thought of as the linear length of the second microchannel (1500) between the second microchannel proximal end (1510) and the second microchannel distal end (1520), may vary greatly. As discussed at length above, in a properly configured microchannel, such as is described above, diffusion is proportional to length, and therefore, the second microchannel length would be determined, by one skilled in the art, to accomplish certain diffusion rate goals. Such linear lengths of the second microchannel (1500) are shown by way of example, and not limitation, in FIGS. 50-53.

As seen well in FIGS. 54-58, in yet another embodiment, as would be known to one skilled in the art, at least one of the first and second diffusion control chamber fluid flow control ports (1350) may further include a section of the first or second, or both, diffusion control chamber sidewall(s) (1320) having a area of reduced thickness (1322) sufficient to minimize formation of a meniscus at the first diffusion control chamber fluid flow control ports (1350) by a liquid within the at least first or second, or both, diffusion control chamber(s) (1300). In yet another embodiment, the area of reduced thickness (1322) may be produced by adhering or otherwise attaching a thin film or membrane to one side of the diffusion control chamber sidewall (1320), and providing a small opening in the film or membrane, consistent with the general structure seen in FIG. 58.

In an illustrative embodiment, shown for example and not limitation and consistent with the structures visualized in FIGS. 54-58, a bioreactor (1010) may have at least one of the diffusion control chamber fluid flow control ports (1350) that blocks the flow of a liquid through the diffusion control chamber fluid flow control port (1350) when the pressure of the liquid is not increased by an external source and there is a difference in viscosity between the liquid in the diffusion control chamber (1300) and a liquid outside of the diffusion control chamber (1300).

Figure 54:
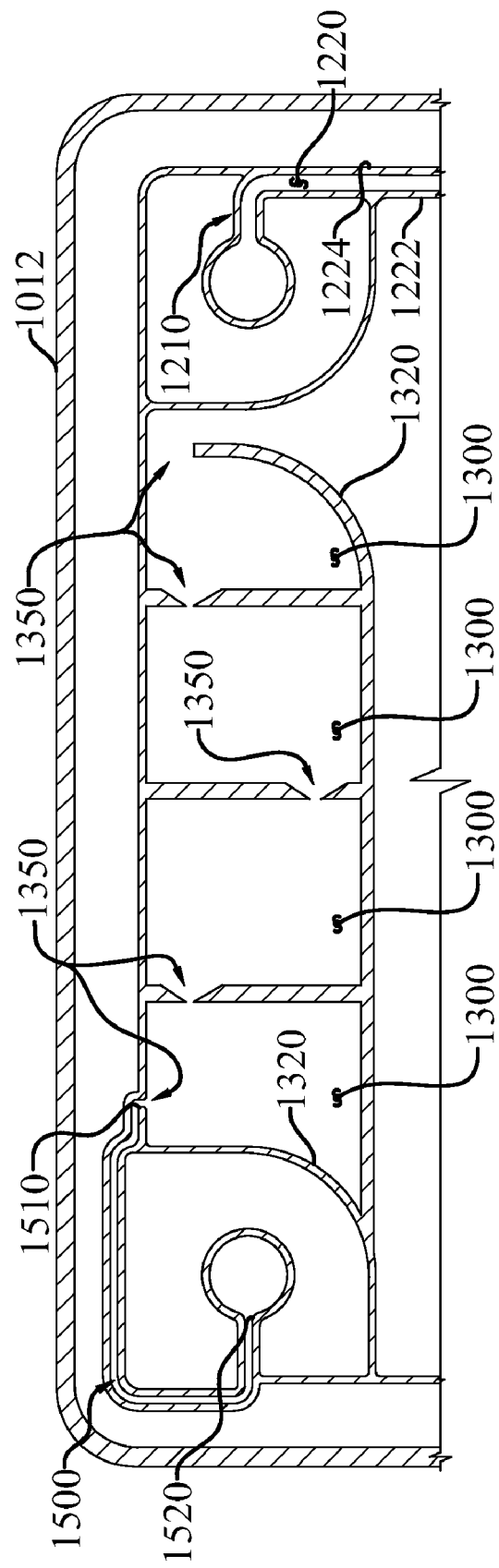
FIG. 54 shows a detail view of the embodiment of the bioreactor shown in FIG. 45 in cross-sectional view.
Figure 55:
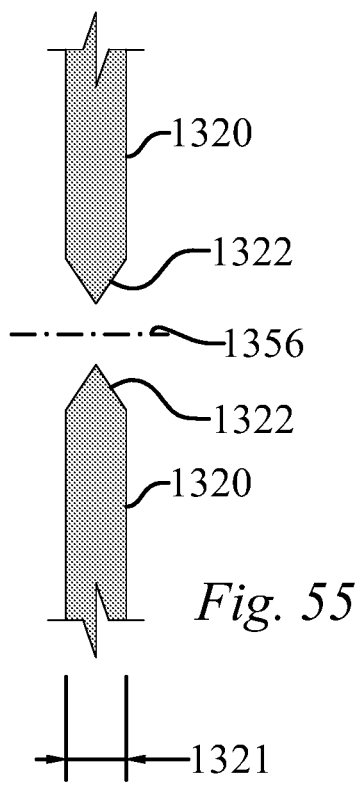
FIG. 55 shows a detail view of an embodiment of the bioreactor of the instant invention in cross-sectional view.
Figure 56:
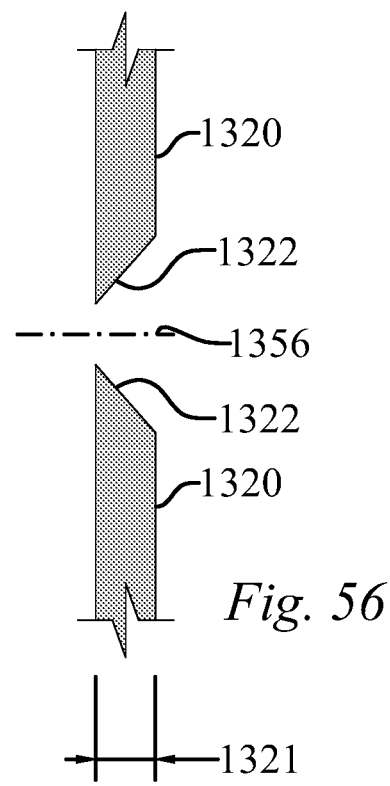
FIG. 56 shows a detail view of an embodiment of the bioreactor of the instant invention in cross-sectional view.
Figure 57:
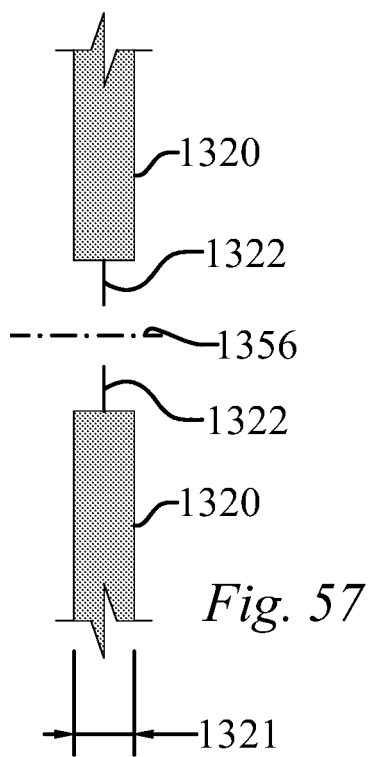
FIG. 57 shows a detail view of an embodiment of the bioreactor of the instant invention in cross-sectional view.
Figure 58:
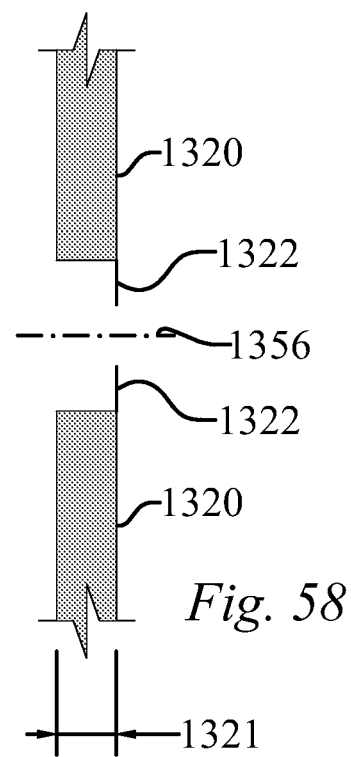
FIG. 58 shows a detail view of an embodiment of the bioreactor of the instant invention in cross-sectional view.

In a further embodiment, such as illustrated in FIG. 54, more than one of the diffusion control chamber fluid flow control ports (1350) further includes a section of the first diffusion control chamber sidewall (1320) having an area of reduced thickness (1322) sufficient to minimize formation of a meniscus at the first fluid flow control port (1350) by a fluid within the first diffusion control chamber (1300). It is specifically intended by this specification that there be no absolute upper limit on the number of diffusion control chamber fluid flow control ports (1350) so configured.

In one or more embodiments, the bioreactor (1010) may have a first diffusion control chamber fluid flow control port (1350) and/or a second fluid diffusion control chamber fluid control port (1350), as seen in FIG. 54, each having a diffusion control chamber fluid flow control port opening axis (1356) orthogonal to the diffusion control chamber sidewall (1320), as seen well in FIGS. 55-58. These axes may be offset by an amount at least equal to a diffusion control chamber sidewall thickness (1321) in at least one of the bioreactor (1010) axes selected from the group of axes consisting of the x-axis, the y-axis, and the z-axis. It may be that offsetting generally opposing fluid diffusion control chamber fluid control ports (1350) may decrease any wave effects within the diffusion control chambers (1300).

In at least one embodiment, seen well in FIGS. 41-42, the bioreactor (1010) may be designed so that the first microchannel (1200) is configured such that when the first microchannel (1200) is at least partially filled with a liquid, the flow of the liquid is laminar and the liquid does not flow out of the second microchannel distal end opening (1522), seen well in FIGS. 50-53, unless the pressure of the liquid is increased by an external source. In various embodiments, the bioreactor (1010) may be configured such that the first microchannel proximal end (1240) blocks the flow of a liquid in the first microchannel (1200) when the pressure of the liquid in the first microchannel (1200) is not increased by an external source and there is a difference in viscosity between the liquid in the first microchannel (1200) and a liquid in the reaction reservoir (1100).

The bioreactor (1010) may further include a filter (1600), seen in FIG. 41 covering the second microchannel distal end opening (1522), and in certain embodiments, the filter (1600) can be an assembly of at least two layers, with a first layer being adapted to prevent the passage of particles having an average size of at least approximately 80 microns, and a second layer being adapted to prevent the passage of particles having an average size of at least approximately 0.2 microns.

In other embodiments, as would be known to one skilled in the art, the bioreactor (1010) may be such that at least a portion of the second microchannel (1500) lies in a non-planar relationship, such as seen in FIGS. 50-53, with at least another portion of the second microchannel (1500) in at least one of the bioreactor (1010) axes selected from the group of axes consisting of the x-axis, the y-axis, and the z-axis.

Figure 59:
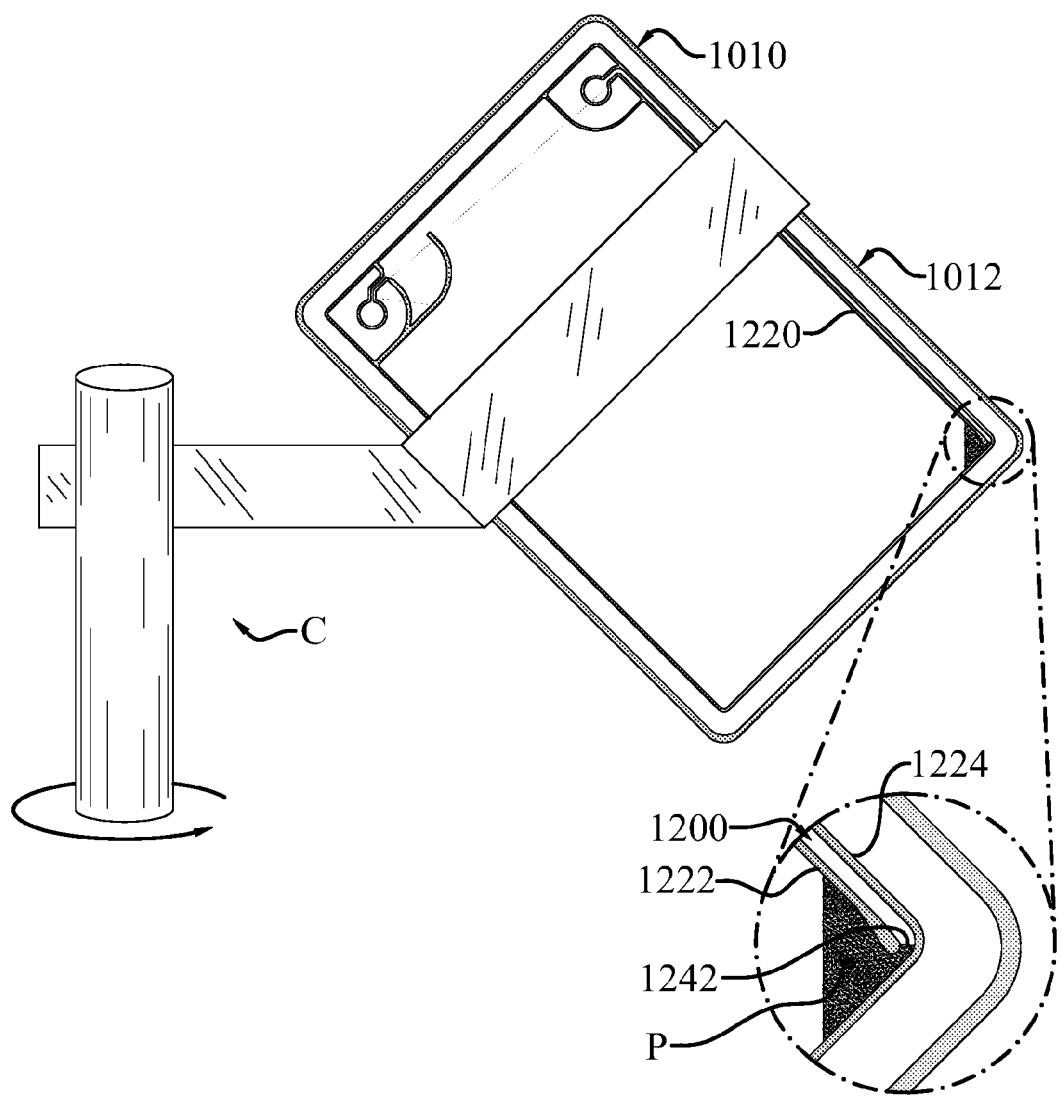
FIG. 59 shows an embodiment of the bioreactor of the instant invention in place within a cell-concentrating centrifuge, and after centrifugation of a cell-concentrate pellet.
Figure 60:
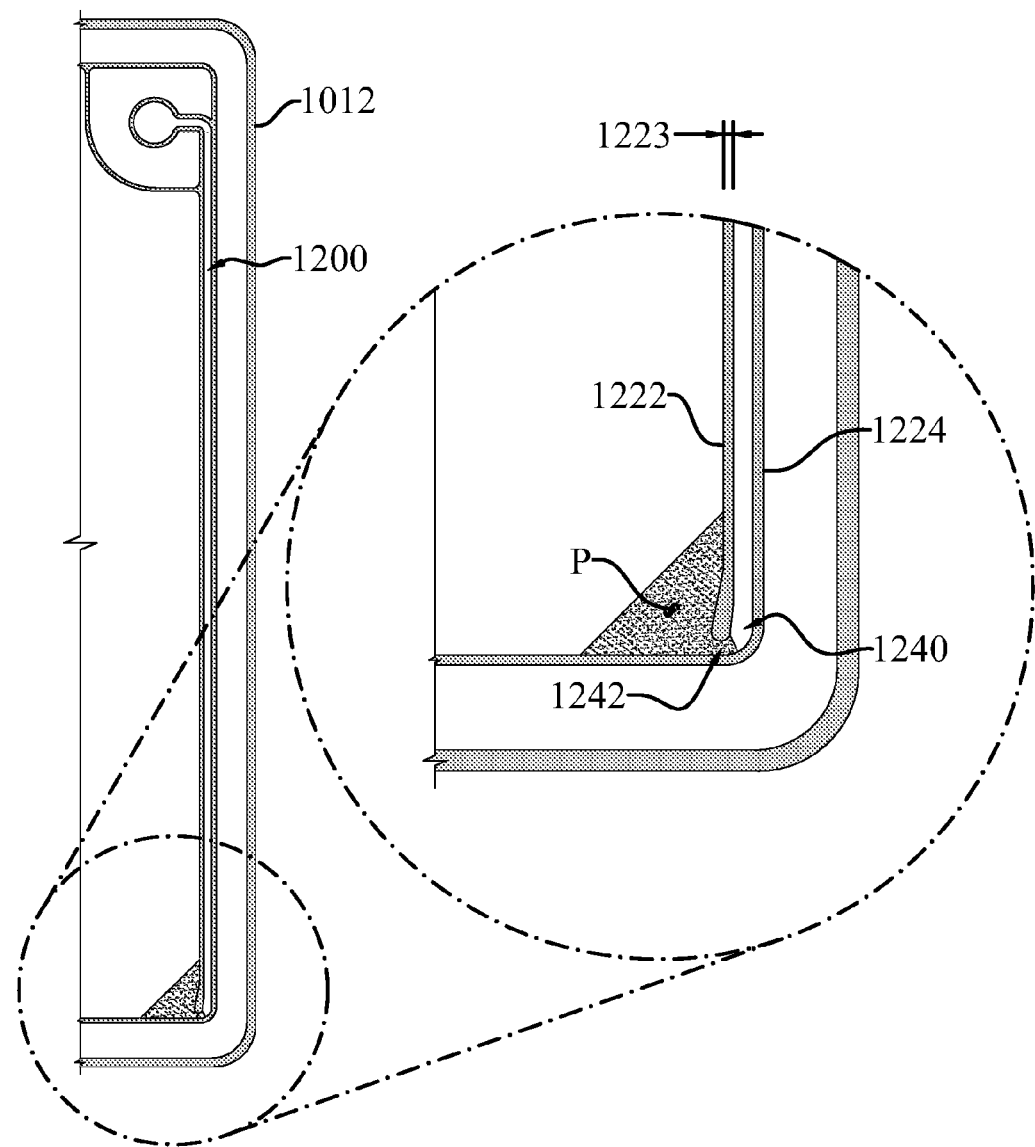
FIG. 60 shows an embodiment of the bioreactor of the instant invention after centrifugation and the production of a cell-concentrate pellet.
Figure 61:
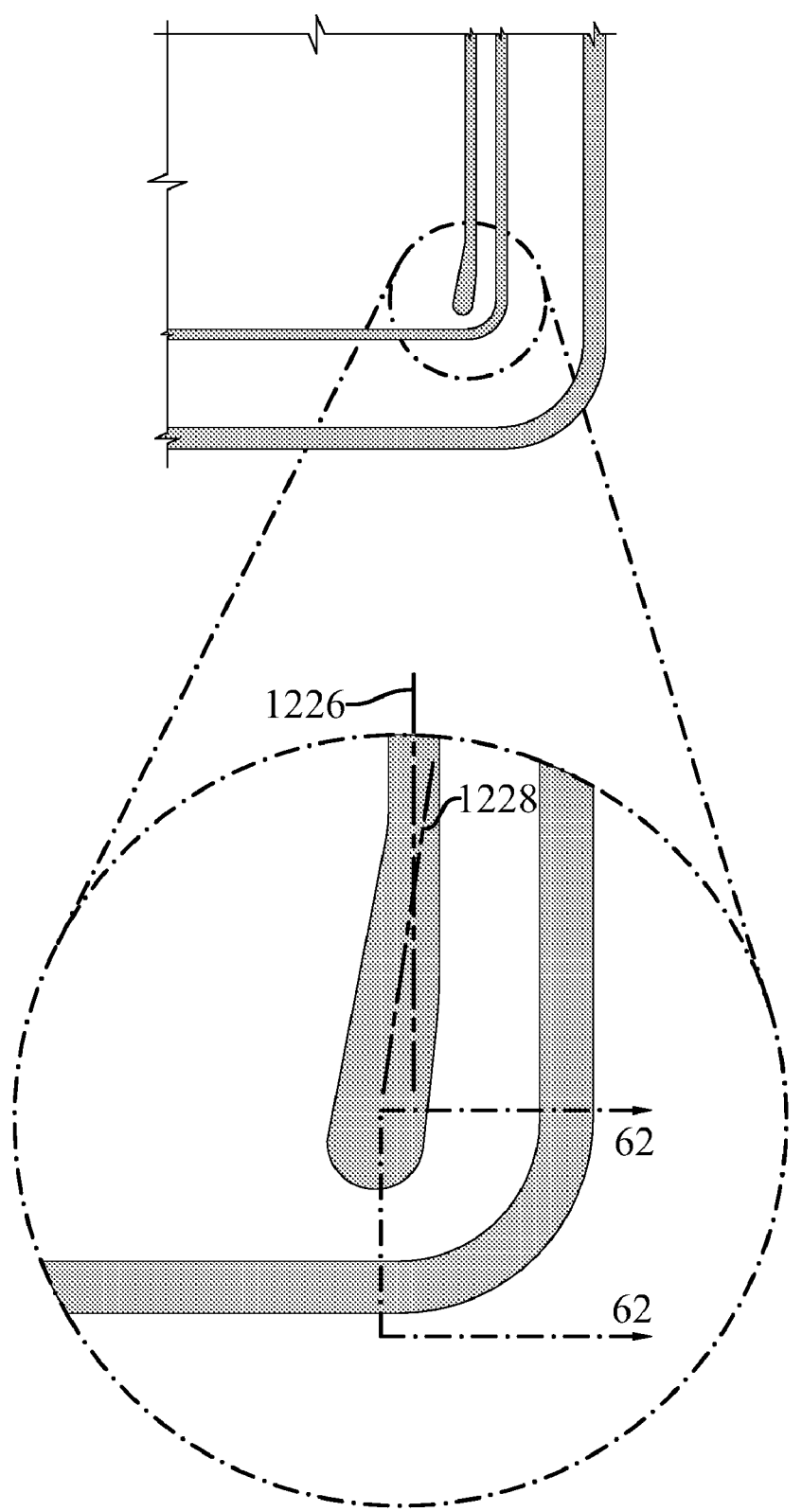
FIG. 61 shows a detail view of an embodiment of the bioreactor of the instant invention in cross-sectional view.

In certain embodiments, and seen well in FIGS. 41-49 and in greater detail in FIGS. 59-61, the bioreactor (1010) may be particularly configured such that the at least a first microchannel medial sidewall (1222) and the at least a first microchannel lateral sidewall (1224) have at least one non-parallel segment. In other embodiments, the at least a first microchannel medial sidewall (1222) has at least a first microchannel medial sidewall first central longitudinal axis (1226) and at least a first microchannel medial sidewall second central longitudinal axis (1228) and these axes diverge by at least three radial degrees. In yet other embodiments, the at least a first microchannel medial sidewall (1222) has more than one medial sidewall thickness (1223). It may be that such conformations assist with removal of cells from the bioreactor (1010) after centrifugation (illustrated as the bioreactor in place within a cell-concentrating centrifuge (C), producing a cell pellet (P), such as illustrated in FIGS. 59 and 60), and make retrograde extraction (aspiration) of cells from a cell pellet (P) through the first microchannel (1200) easier.

Certain ratios of size between various structures have been found to be useful. In one embodiment, the at least one first microchannel proximal end-reaction reservoir fenestration height (1244) is not more than 2.5 times the at least one first microchannel proximal end-reaction reservoir fenestration width (1246). In another embodiment, the at least one first microchannel proximal end-reaction reservoir fenestration height (1244) is not less than 0.9 times the at least one first microchannel proximal end-reaction reservoir fenestration width (1246). In yet another embodiment, the at least one first microchannel proximal end-reaction reservoir fenestration cross-sectional area is not less than 0.60 mm².

Various structural areas and volumes have also been found useful. In one embodiment, the at least one reaction reservoir sidewall (1120) has a total surface area of between 100 cm² and 200 cm². In another embodiment, the reaction reservoir volume is between 15 ml and 25 ml.

Figure 64:
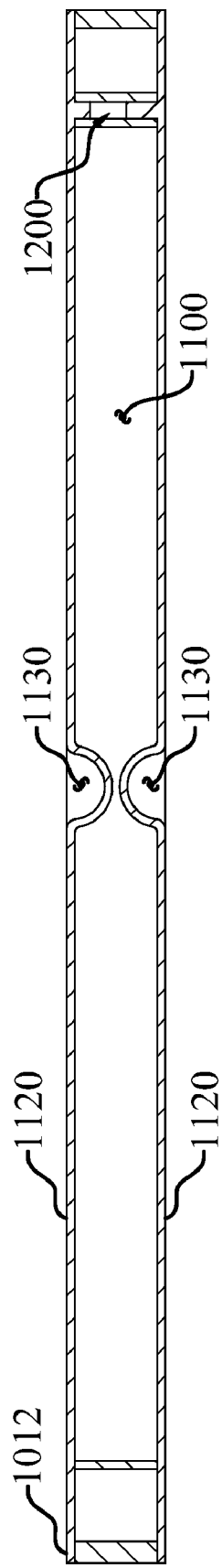
FIG. 64 shows a detail view of an embodiment of the bioreactor of the instant invention in cross-sectional view.

In certain embodiments, such as seen in FIGS. 41 and 64, the at least one reaction reservoir sidewall (1120) further comprises at least one anti-collapse button (1130) on an interior surface of the reaction reservoir sidewall (1120). In some embodiments, two opposed anti-collapse buttons (1130), seen in FIG. 64, are found on opposing interior surfaces of the reaction reservoir (1100).

Figure 62:
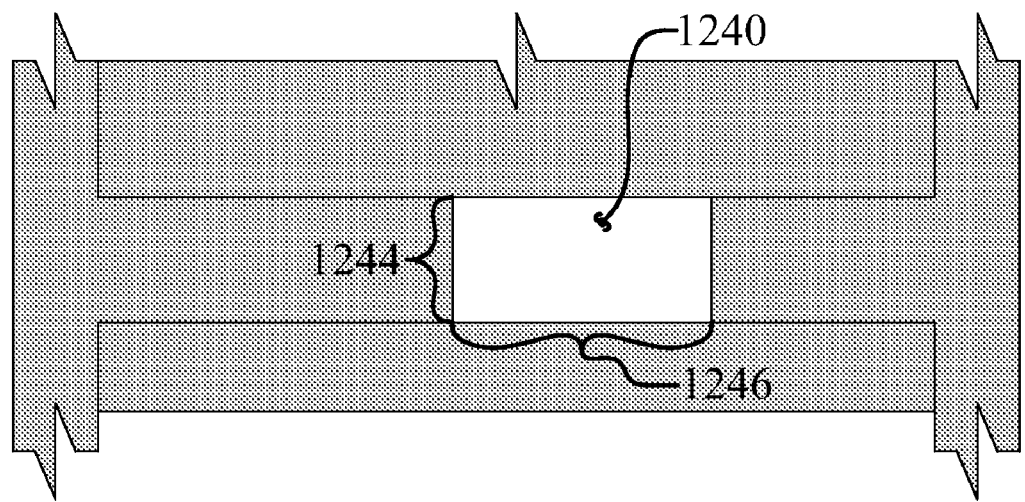
FIG. 62 shows a detail view of an embodiment of the bioreactor of the instant invention as viewed across section line 62-62 in FIG. 61.
Figure 63:
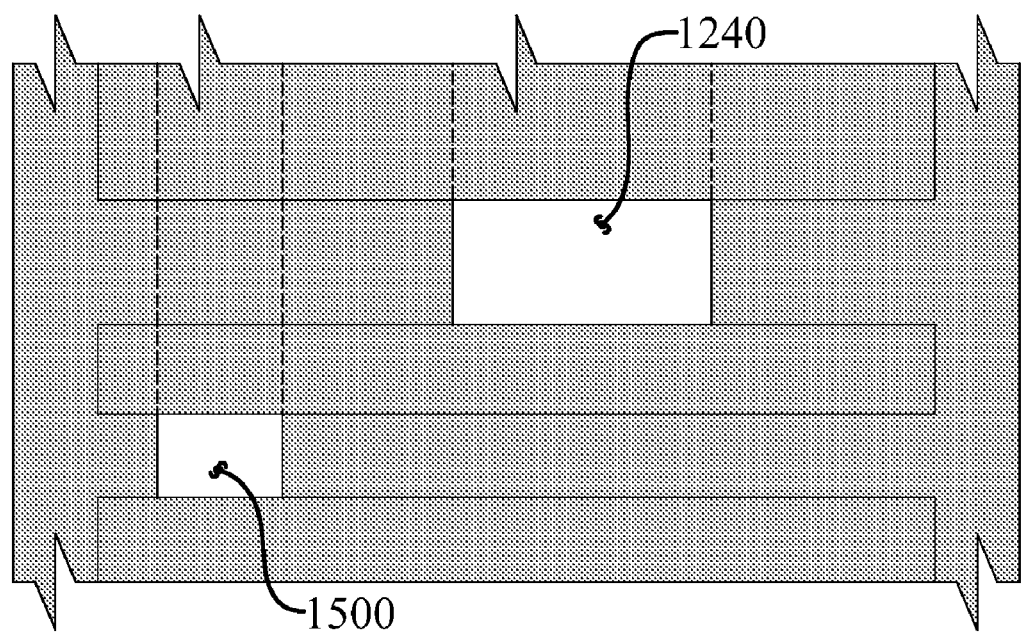
FIG. 63 shows a detail view of an embodiment of the bioreactor of the instant invention as viewed across section line 63-63 in FIG. 48.

One skilled in the art will realize that a wide array of possibilities exists for the spatial location of various structures within the bioreactor (1010). In one embodiment, at least a portion of the first microchannel (1200) is fully embedded within the frame (1012), as seen in FIGS. 62-64. Such construction may make structures such as the first microchannel (1200) more dimensionally stable and simplify molding processes.

In yet another group of embodiments, as seen in FIGS. 41-64, a bioreactor (1010) may have a continuous fluid path, beginning with a first microchannel (1200) having a first microchannel distal end (1210) and a first microchannel proximal end (1240), and thence through at least the following structures: a reaction reservoir (1100), a first diffusion control chamber control port (1350), a diffusion control chamber (1300), a second diffusion control chamber control port (1350), and a second microchannel (1500), having a second microchannel proximal end (1510) and a second microchannel distal end (1520). In such embodiments, it may be useful to have, in at least one of the diffusion control chamber ports (1350) selected from the group consisting of the first diffusion control chamber port (1350) and the second diffusion control chamber port (1350), one or more diffusion control chamber ports (1350) that block the flow of a liquid through the diffusion control chamber fluid flow control port (1350) when the pressure of the liquid is not increased by an external source and there is a difference in viscosity between the liquid in the diffusion control chamber (1300) and a liquid outside of the diffusion control chamber (1300).

In yet other embodiments that would be known to one skilled in the art, and also as seen in FIGS. 41-64, a bioreactor (1010) may have at least one reaction reservoir (1100) in liquid communication with at least one diffusion control chamber (1300) that is in fluid communication with an ambient atmosphere. Additionally, the reaction reservoir (1100) may be formed such that it is not in liquid communication with an ambient atmosphere when the pressure of a liquid in the diffusion control chamber (1300) is not increased by an external source or there is a difference in viscosity between the liquid in the diffusion control chamber (1300) and a fluid in the ambient atmosphere. The open fluid communication allows the passage of gaseous fluids in and out of the reaction reservoir (1100), while the restrictions on liquid communication make it less likely for the bioreactor (1010) to leak, even when turned in various directions.

Numerous alterations, modifications, and variations of the preferred embodiments disclosed herein will be apparent to those skilled in the art and they are all anticipated and contemplated to be within the spirit and scope of the bioreactor (1010). For instance, it is understood that the specification of a first fluid, a second fluid, and a third fluid are for illustration, and not limitation, only. The fluids may all be of the same composition, or may be different. Additionally, the illustration of particular features in various embodiments is for illustration, and not limitation, only. Any or all of the various features of the bioreactor (1010) may be combined in various illustrated and non-illustrated embodiments, as would be known to one skilled in the art. Further, although specific embodiments have been described in detail, those with skill in the art will understand that the preceding embodiments and variations can be modified to incorporate various types of substitute and or additional or alternative materials, relative arrangement of elements, and dimensional configurations. Accordingly, even though only few variations of the bioreactor (1010) are described herein, it is to be understood that the practice of such additional modifications and variations and the equivalents thereof, are within the spirit and scope of the bioreactor (1010) as defined in the following claims. The corresponding structures, materials, acts, and equivalents of all means or step plus function elements in the claims below are intended to include any structure, material, or acts for performing the functions in combination with other claimed elements as specifically claimed.

I claim:

1. A bioreactor (1010), comprising,
a plurality of fluid-filled structures having three-dimensional relationships among the structures defined in terms of an orthogonally related bioreactor (1010) x axis, y axis, and z axis, bounded within an external frame (1012), and further comprising:
at least a first microchannel (1200) having a first microchannel distal end (1210) and a first microchannel distal end opening (1212), at least a first microchannel medial sidewall (1222) and at least a first microchannel lateral sidewall (1224), a first microchannel cross-sectional area, and a first microchannel proximal end (1240);
a reaction reservoir (1100) having at least one reaction reservoir sidewall (1120) and a reaction reservoir volume, in fluid communication with the first microchannel proximal end (1240) through a first microchannel proximal end-reaction reservoir fenestration (1242), having at least one first microchannel proximal end-reaction reservoir fenestration height (1244) and at least one first microchannel proximal end-reaction reservoir fenestration width (1246) defining at least one first microchannel proximal end-reaction reservoir fenestration cross-sectional area;
at least one diffusion control chamber (1300) having at least one first diffusion control chamber sidewall (1320) and a first diffusion control chamber volume, in fluid communication with the reaction reservoir (1100) through at least a first diffusion control chamber fluid flow control port (1350),
at least a second microchannel (1500) having a second microchannel proximal end (1510), a second microchannel distal end (1520), a second microchannel length and a second microchannel cross-sectional area, in fluid communication with the at least one diffusion control chamber (1300) through at least a second diffusion control chamber fluid flow control port (1350) having a cross-sectional area lesser than the second microchannel cross-sectional area and in fluid communication with an ambient atmosphere through the second microchannel proximal end (1520), and
wherein the at least one diffusion control chamber (1300) further comprises at least a first diffusion control chamber (1300) and a second diffusion control chamber (1300) wherein the first diffusion control chamber (1300) has at least a first diffusion control chamber fluid flow control port (1350) and at least a second diffusion control chamber fluid flow control port (1350).

2. The bioreactor (1010) according to claim 1, wherein at least one of the first and second diffusion control chamber fluid flow control ports (1350) further comprises a section of the first diffusion control chamber sidewall (1320) having an area of reduced thickness (1322) sufficient to minimize formation of a meniscus at the first diffusion control chamber fluid flow control ports (1350) by a liquid within the at least first diffusion control chamber (1300).

3. The bioreactor (1010) according to claim 1, wherein at least one of the diffusion control chamber fluid flow control ports (1350) blocks the flow of a liquid through the diffusion control chamber fluid flow control port (1350) when the pressure of the liquid is not increased by an external source and there is a difference in viscosity between the liquid in the diffusion control chamber (1300) and a liquid outside of the diffusion control chamber (1300).

4. The bioreactor (1010) according to claim 1, wherein more than one of the diffusion control chamber fluid flow control ports (1350) further includes a section of the first diffusion control chamber sidewall (1320) having an area of reduced thickness (1322) sufficient to minimize formation of a meniscus at the first fluid flow control port (1350) by a fluid within the first diffusion control chamber (1300).

5. The bioreactor (1010) according to claim 1, wherein the first diffusion control chamber fluid flow control port (1350) and the second fluid diffusion control chamber fluid control port (1350) each have a diffusion control chamber fluid flow control port opening axis (1356) orthogonal to the diffusion control chamber sidewall (1320) and these axes are offset by an amount at least equal to a diffusion control chamber sidewall thickness (1321) in at least one of the bioreactor (1010) axes selected from the group of axes consisting of the x axis, the y axis, and the z axis.

6. The bioreactor (1010) according to claim 1, wherein the first microchannel (1200) is configured such that when the first microchannel (1200) is at least partially filled with a fluid, the flow of the fluid is laminar and the fluid does not flow out of the second microchannel distal end opening (1522) unless the pressure of the fluid is increased by an external source.

7. The bioreactor (1010) according to claim 1, wherein the first microchannel proximal end (1240) blocks the flow of a fluid in the first microchannel (1200) when the pressure of the fluid in the first microchannel (1200) is not increased by an external source and there is a difference in viscosity between the fluid in the first microchannel (1200) and a fluid in the reaction reservoir (1100).

8. The bioreactor (1010) according to claim 1, wherein at least a portion of the second microchannel (1500) lies in a non-planar relationship with at least another portion of the second microchannel (1500) in at least one of the bioreactor (1010) axes selected from the group of axes consisting of the x axis, the y axis, and the z axis.

9. The bioreactor (1010) according to claim 1, wherein the at least a first microchannel medial sidewall (1222) and the at least a first microchannel lateral sidewall (1224) have at least one non-parallel segment.

10. A bioreactor (1010) having a continuous fluid path, beginning with a first microchannel (1200) having a first microchannel distal end (1210) and a first microchannel proximal end (1240), and thence through at least the following structures, a reaction reservoir (1100), a first diffusion control chamber control port (1350), a diffusion control chamber (1300), a second diffusion control chamber control port (1350), a second diffusion control chamber (1300) and a second microchannel (1500) having a cross-sectional area greater than a cross-sectional area of the second diffusion control chamber control port (1350), having a second microchannel proximal end (1510) and a second microchannel distal end (1520) in communication with an ambient atmosphere; wherein at least one of the diffusion control chamber ports (1350) selected from the group consisting of the first diffusion control chamber port (1350) and the second diffusion control chamber port (1350), blocks the flow of a liquid through the diffusion control chamber fluid flow control port (1350) in the absence of a pressure differential in the liquid across the diffusion control chamber fluid flow control port (1350) and there is a difference in viscosity between the liquid in the diffusion control chamber (1300) and a liquid outside of the diffusion control chamber (1300).

11. A bioreactor (1010), comprising, a plurality of fluid-filled structures having three-dimensional relationships among the structures defined in terms of an orthogonally related bioreactor (1010) x axis, y axis, and z axis, bounded within an external frame (1012), and further comprising:

at least a first microchannel (1200) having a first microchannel distal end (1210) and a first microchannel distal end opening (1212), at least a first microchannel medial sidewall (1222) and at least a first microchannel lateral sidewall (1224), a first microchannel cross-sectional area, and a first microchannel proximal end (1240);

a reaction reservoir (1100) having at least one reaction reservoir sidewall (1120) and a reaction reservoir volume, in fluid communication with the first microchannel proximal end (1240) through a first microchannel proximal end-reaction reservoir fenestration (1242), having at least one first microchannel proximal end-reaction reservoir fenestration height (1244) and at least one first microchannel proximal end-reaction reservoir fenestration width (1246) defining at least one first microchannel proximal end-reaction reservoir fenestration cross-sectional area;

at least one diffusion control chamber (1300) having at least one first diffusion control chamber sidewall (1320) and a first diffusion control chamber volume, in fluid communication with the reaction reservoir (1100) through at least a first diffusion control chamber fluid flow control port (1350), and at least a second microchannel (1500) having a second microchannel proximal end (1510), a second microchannel distal end (1520), a second microchannel length and a second microchannel cross-sectional area, in fluid communication with the at least one diffusion control chamber (1300) through at least a second diffusion control chamber fluid flow control port (1350) having a cross-sectional area lesser than the second microchannel cross-sectional area and in fluid communication with an ambient atmosphere through the second microchannel proximal end (1520); and wherein at least a portion of the second microchannel (1500) lies in a non-planar relationship with at least another portion of the second microchannel (1500) in at least one of the bioreactor (1010) axes selected from the group of axes consisting of the x axis, the y axis, and the z axis.

12. The bioreactor (1010) according to claim 11, wherein the at least one diffusion control chamber (1300) further comprises at least a first diffusion control chamber (1300) and a second diffusion control chamber (1300) wherein the first diffusion control chamber (1300) has at least a first diffusion control chamber fluid flow control port (1350) and at least a second diffusion control chamber fluid flow control port (1350).

13. The bioreactor (1010) according to claim 11, wherein at least one of the first and second diffusion control chamber fluid flow control ports (1350) further comprises a section of the first diffusion control chamber sidewall (1320) having an area of reduced thickness (1322) sufficient to minimize formation of a meniscus at the first diffusion control chamber fluid flow control ports (1350) by a liquid within the at least first diffusion control chamber (1300).

14. The bioreactor (1010) according to claim 11, wherein at least one of the diffusion control chamber fluid flow control ports (1350) blocks the flow of a liquid through the diffusion control chamber fluid flow control port (1350) when the pressure of the liquid is not increased by an external source and there is a difference in viscosity between the liquid in the diffusion control chamber (1300) and a liquid outside of the diffusion control chamber (1300).

15. The bioreactor (1010) according to claim 11, wherein more than one of the diffusion control chamber fluid flow control ports (1350) further includes a section of the first diffusion control chamber sidewall (1320) having an area of reduced thickness (1322) sufficient to minimize formation of a meniscus at the first fluid flow control port (1350) by a fluid within the first diffusion control chamber (1300).

16. The bioreactor (1010) according to claim 11, wherein the first diffusion control chamber fluid flow control port (1350) and the second fluid diffusion control chamber fluid control port (1350) each have a diffusion control chamber fluid flow control port opening axis (1356) orthogonal to the diffusion control chamber sidewall (1320) and these axes are offset by an amount at least equal to a diffusion control chamber sidewall thickness (1321) in at least one of the bioreactor (1010) axes selected from the group of axes consisting of the x axis, the y axis, and the z axis.

17. The bioreactor (1010) according to claim 11, wherein the first microchannel (1200) is configured such that when the first microchannel (1200) is at least partially filled with a fluid, the flow of the fluid is laminar and the fluid does not flow out of the second microchannel distal end opening (1522) unless the pressure of the fluid is increased by an external source.

18. The bioreactor (1010) according to claim 11, wherein the first microchannel proximal end (1240) blocks the flow of a fluid in the first microchannel (1200) when the pressure of the fluid in the first microchannel (1200) is not increased by an external source and there is a difference in viscosity between the fluid in the first microchannel (1200) and a fluid in the reaction reservoir (1100).

19. The bioreactor (1010) of claim 11, further comprising a filter (1600) covering the second microchannel distal end opening (1522) wherein the filter (1600) further includes an assembly of at least two layers with a first layer being adapted to prevent the passage of particles having an average size of at least approximately 80 microns, and a second layer being adapted to prevent the passage of particles having an average size of at least approximately 0.2 microns.

20. The bioreactor (1010) according to claim 11, wherein the at least a first microchannel medial sidewall (1222) and the at least a first microchannel lateral sidewall (1224) have at least one non-parallel segment.

21. The bioreactor (1010) according to claim 11, wherein the at least a first microchannel medial sidewall (1222) has at least a first microchannel medial sidewall first central longitudinal axis (1226) and at least a first microchannel medial sidewall second central longitudinal axis (1228) and these axes diverge by at least three radial degrees.

22. The bioreactor (1010) according to claim 11, wherein the at least a first microchannel medial sidewall (1222) has more than one medial sidewall thickness (1223).

* * * * *